United States Patent [19]

Rohr et al.

[11] 4,373,105

[45] Feb. 8, 1983

[54] M-ANILIDE-URETHANES

[75] Inventors: Wolfgang Rohr, Mannheim; Ulrich Schirmer, Heidelberg; Bruno Wuerzer, Otterstadt, all of Fed. Rep. of Germany

[73] Assignee: BASF Aktiengesellschaft, Fed. Rep. of Germany

[21] Appl. No.: 242,558

[22] Filed: Mar. 11, 1981

Related U.S. Application Data

[63] Continuation of Ser. No. 86,134, Oct. 18, 1979, abandoned.

[30] Foreign Application Priority Data

Oct. 26, 1978 [DE] Fed. Rep. of Germany ....... 2846625

[51] Int. Cl.³ .................. C07C 155/08; C07C 155/02; C07C 155/03; C07C 125/065

[52] U.S. Cl. .......................................... 560/27; 71/86; 71/88; 71/90; 71/91; 71/92; 71/94; 71/95; 71/98; 71/100; 71/103; 71/104; 71/105; 71/111; 260/454; 260/455 A; 260/465 D; 560/9; 560/10; 560/13; 560/18; 560/21; 560/22; 560/24; 560/28; 560/29; 560/30; 560/31; 560/32; 560/33; 564/162; 564/175; 564/214

[58] Field of Search .................. 560/27, 9, 13, 21, 28; 260/455 A, 465 D, 454

[56] References Cited

U.S. PATENT DOCUMENTS 4,013,450 3/1977 Olin et al. .............................. 560/27

Primary Examiner—Michael L. Shippen
Attorney, Agent, or Firm—Keil & Witherspoon

[57] ABSTRACT

New m-anilide-urethanes, processes for their manufacture, herbicides containing these compounds, and processes for controlling unwanted plant growth with these compounds.

3 Claims, No Drawings

M-ANILIDE-URETHANES

This is a continuation of application Ser. No. 086,134, filed Oct. 18, 1979 now abandoned.

The present invention relates to new m-anilide-urethanes, processes for their manufacture, herbicides containing these compounds, and processes for controlling unwanted plant growth with these compounds.

It has been disclosed (German Pat. No. 1,542,836) that important, commercially available herbicides such as 3-isopropyl-2,1,3-benzothiadiazinone-(4)-2,2-dioxide are, in spite of their excellent action on many weed species, ineffective against a number of important unwanted plants. By contrast, m-anilidoureas, e.g., 2,4-dichlorophenoxyacetic acid-(3'-(N'-methylureido)-anilide, do have a somewhat broader spectrum of action, combating broadleaved and grassy weeds, but the literature gives no indication of a pronounced tolerance by crop plants, which would enable them to be used as selective herbicidal agents (German Printed Application DE-AS No. 1,793,226).

U.S. Pat. No. 3,979,202 discloses numerous 3'-(carbamoyloxy)-anilides, e.g., 3'-N-isopropylcarbamoyloxypropionanilide, which have widely varying herbicidal actions on higher plants-they may be used as herbicides or as agents for reducing the height of crop plants, and at rates of from 0.1 to 10 lbs of active ingredient per acre.

We have now found that m-anilide-urethanes of the formula

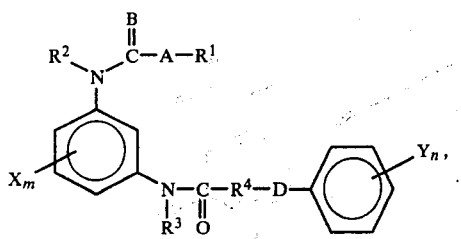

where A, B and D are identical or different and each denotes oxygen or sulfur, $R^1$ denotes unsubstituted alkyl; alkyl substituted by halogen, alkoxy, alkoxycarbonyl or cyano; unsubstituted or halogen-substituted alkenyl; unsubstituted or halogen- or alkoxy-substituted alkynyl; or $R^1$ denotes unsubstituted or alkyl-substituted cycloalkyl or aryl, $R^2$ and $R^3$ are identical or different and each denotes hydrogen, alkyl, alkoxyalkyl or haloalkyl, $R^4$ denotes alkylene of 1 to 6 carbon atoms which is unsubstituted or substituted by alkyl, alkoxyalkyl or haloalkyl, X denotes hydrogen, alkyl, haloalkyl, alkoxy, halogen, nitro or amino, Y denotes hydrogen, alkyl, haloalkyl, alkoxyalkyl, cycloalkyl, aralkyl, halogen, an alkenyl chain fused with the benzene ring to give a substituted or unsubstituted naphthyl ring, Y further denotes alkoxy, haloalkoxy, alkylthio, nitro, aryl, thiocyanato, cyano,

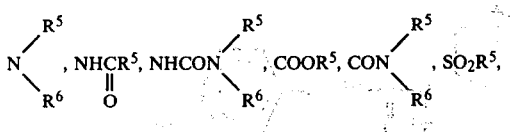

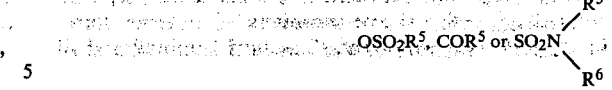

$R^5$ and $R^6$ being identical or different and each denoting hydrogen or having the meanings given for $R^1$, m denotes one of the integers 1, 2, 3 and 4, and n denotes one of the integers 1, 2, 3, 4 and 5, have a good herbicidal action on numerous important unwanted plants. They are tolerated by various crop plants without, or with only very minor, damage.

The radicals in the general formula may for instance have the following meanings:

$R^1$: unsubstituted alkyl, or alkyl substituted by halogen, alkoxy, alkoxycarbonyl or cyano (e.g., methyl, ethyl, 2-chloroethyl, 2-methoxyethyl, methoxycarbonylmethyl, isopropyl, n-propyl, n-butyl, sec-butyl, tert-butyl, isobutyl, cyanomethyl), unsubstituted or halogen-substituted alkenyl (e.g., allyl, 2-chloropropen-(1)-yl-(3), buten-(1)-yl-(3)), unsubstituted or halogen- or alkoxy-substituted alkynyl (e.g., propargyl, butyn-(1)-yl-(3), 1-chlorobutyn-(2)-yl-(4)), unsubstituted or alkyl-substituted cycloalkyl (e.g., cyclopentyl, cyclohexyl, 3-methylcyclohexyl, 2,6-dimethylcyclohexyl, cycloheptyl, 4-tert-butylcyclohexyl), or aryl (e.g., phenyl);

$R^2$ and $R^3$, independently of each other: hydrogen, alkyl (e.g., methyl, ethyl, isopropyl), alkoxyalkyl (e.g., methoxymethyl, 2-methoxyethyl), or haloalkyl (e.g., chloromethyl, 2-chloroethyl);

$R^4$: alkylene of 1 to 6 carbon atoms which is unsubstituted or substituted by alkyl, alkoxyalkyl or haloalkyl (e.g., methylene, methylmethylene, dimethylmethylene, propylene, hexylene, chloromethylmethylene, methoxymethylmethylene, ethylmethylene, methylethylene, isopropylmethylene, 1-chloromethylethylene, methoxyethylmethylene, 2-chloroethylmethylene, diethylmethylene, ethylene, methylpropylene, butylene, dimethylethylene, propylmethylene);

X: hydrogen, alkyl (e.g., methyl), haloalkyl (e.g., trifluoromethyl), alkoxy (e.g., methoxy), halogen (e.g., fluorine, chlorine, bromine and iodine), nitro or amino;

Y: hydrogen, alkyl (e.g., methyl, isopropyl), haloalkyl (e.g., trifluoromethyl), alkoxyalkyl (e.g., methoxymethyl), cycloalkyl (e.g., cyclohexyl), aralkyl (e.g., benzyl), halogen (e.g., fluorine, chlorine, bromine and iodine), an alkenyl chain which is fused with the benzene ring to give a substituted or unsubstituted naphthyl ring, alkoxy (e.g., methoxy), haloalkoxy (e.g., trifluoromethoxy), alkylthio (e.g., methylthio), nitro, aryl (e.g., phenyl), thiocyanato, cyano,

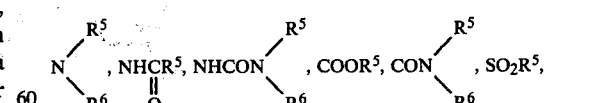

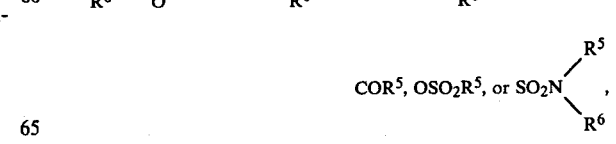

$R^5$ and $R^6$ being identical or different and each denoting hydrogen or having the meanings given for $R^1$.

The new compounds may be prepared for instance by the following methods, A, B, D, $R^1$, $R^2$, $R^3$, $R^4$, X, Y, m and n having the above meanings. The terms "urethanes" and "chloroformates" as used hereinafter shall also cover thiono-, thio- and dithiourethanes, and chloroformic acid thionoesters, chloroformic acid thioesters and chloroformic acid dithioesters.
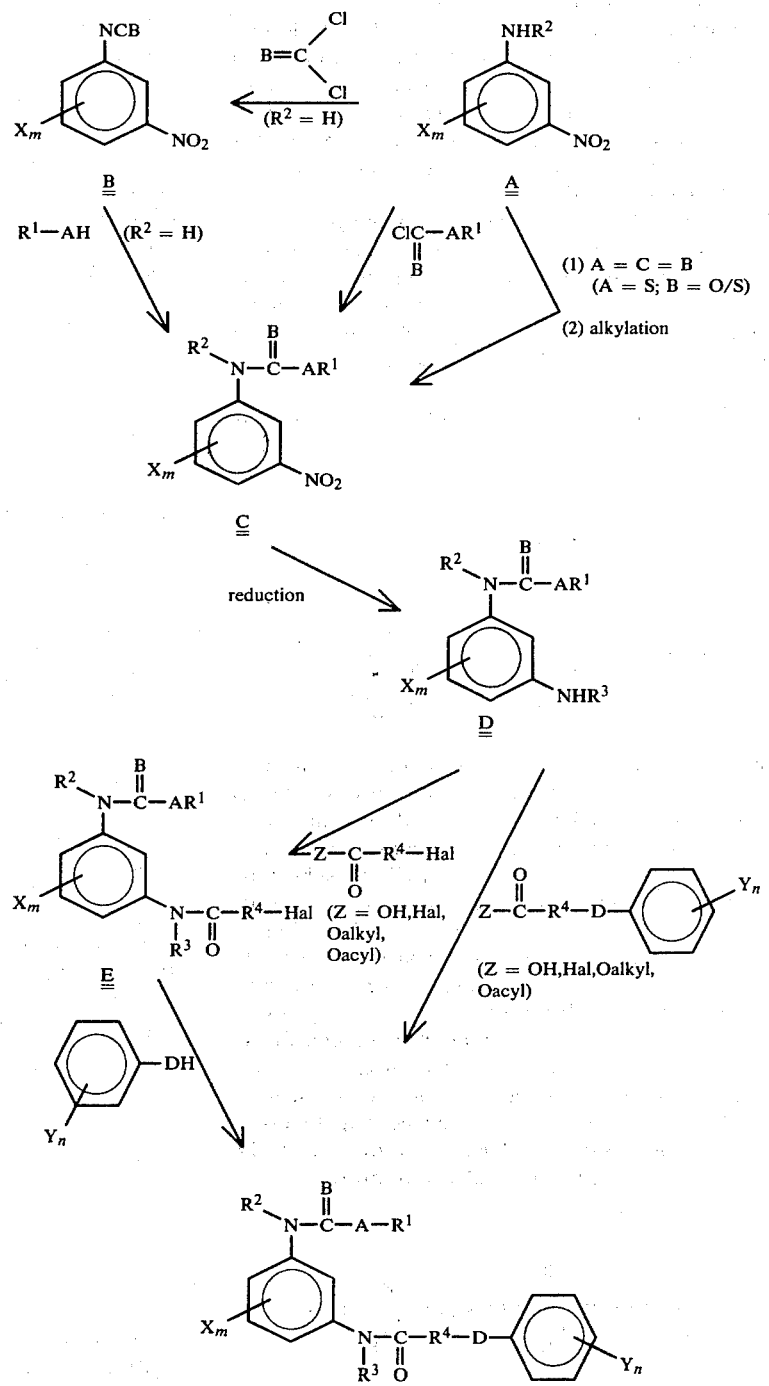

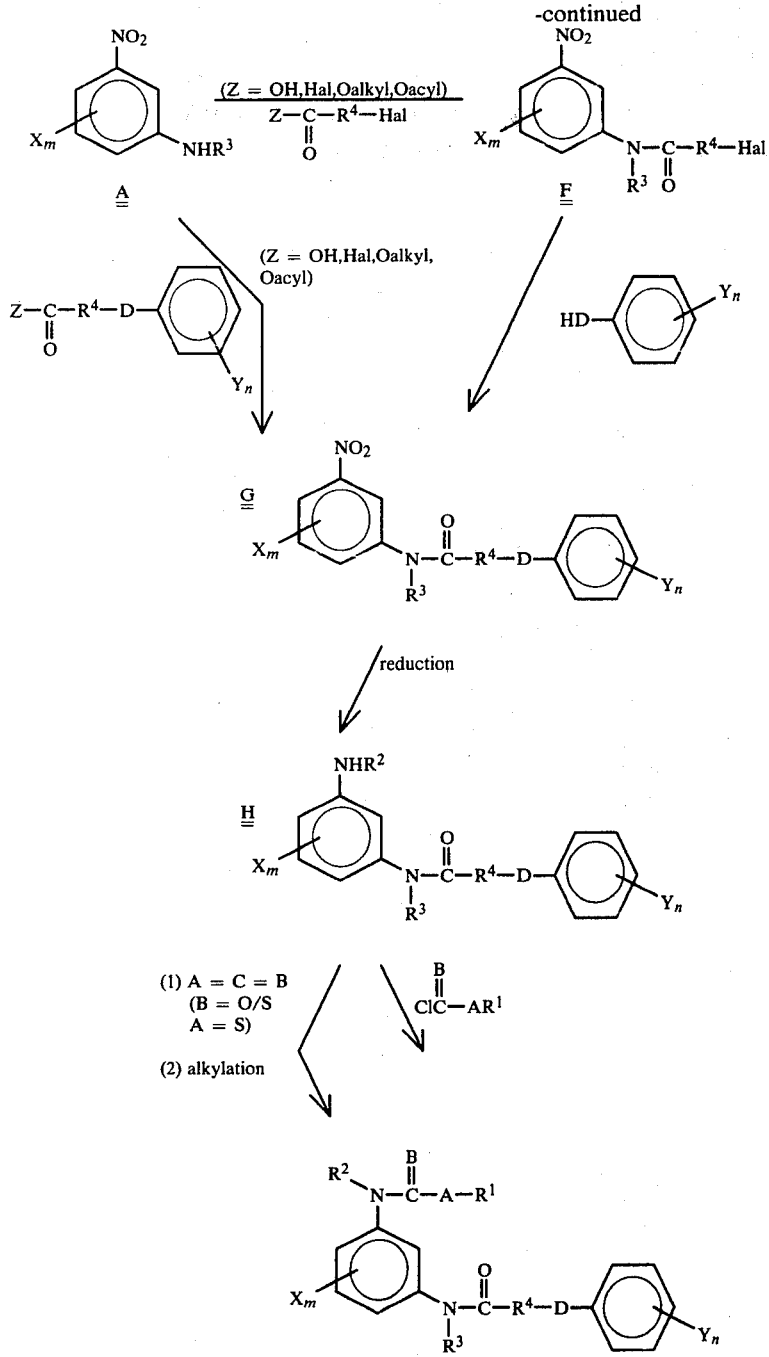

It will be clear from the foregoing diagrams how interrelated the starting materials are. It will also be apparent that, depending on the nature of the substituents A, B, D, $R^1$, $R^2$, $R^3$, $R^4$, X and Y and on the availability of the reactants, one route may be more advantageous than another.

Starting from prior art m-nitranilines (A), m-nitrophenyl iso(thio)-cyanates (B) may be prepared (W. Siefken, J. Liebigs Annalen der Chemie, 562, 75 et seq., 1949), which in turn smoothly react with the components $R^1$-AH to give the nitro(thio)urethanes (C) (S. Petersen, Methoden der Organ. Chemie, VIII, 131 Georg-Thieme-Verlag, Stuttgart, 4th ed., 1952), which, however, are also directly accessible from m-nitranilines (A) with chloroformates ($R^1$A-CB-Cl) (German Laid-Open Application DE-OS No. 1,643,763) or with carbon disulfide or carbon oxysulfide, base and alkylating agent (Methoden der Organ. Chemie, IX, 831 et seq., Georg-Thieme-Verlag, Stuttgart, 4th ed., 1955). Reduction then gives the aminourethanes (D, $R^3$=H), (S. Schröter, Methoden der Organ. Chemie, XI/1, 350 et seq., Georg-Thieme-Verlag, Stuttgart, 4th ed., 1957), which are acylated, either direct or after conversion to the product monosubstituted on the amino nitrogen (D, $R^3 \neq H$) (Methoden der Organ. Chemie, XI/1, 24 et seq., Georg-Thieme-Verlag, Stuttgart, 4th ed., 1957), with phenoxycarboxylic acids, phenoxycarboxylic acid halides, esters or anhydrides to give the m-anilide-urethanes according to the invention (Methoden der Organ. Chemie, XI/2, 3 et seq., Georg-Thieme-Verlag, Stuttgart, 4th ed., 1958).

The aminourethanes (D) may also first be reacted with a halocarboxylic acid, halocarboxylic acid halide, ester or anhydride to give the m-anilide-urethanes (E), which then react with phenols or thiophenols to give the m-anilide-urethanes according to the invention (Methoden der Organ. Chemie, VI/3, 54 et seq., Georg-Thieme-Verlag, Stuttgart, 4th ed., 1965).

A further synthesis route is to react m-nitroanilines (A) with phenoxycarboxylic acids, phenoxycarboxylic acid halides, esters or anhydrides to give m-nitroanilides (G), which are also accessible via nitrohalides (F).

Reduction of the m-nitroanilides (G) gives the m-aminoanlides (H, $R^2=H$), which may be reacted, either directly or after conversion to the product monosubstituted on the amino nitrogen (H, $R^2 \neq H$), with chloroformates ($R^1ACB-Cl$) or with carbon disulfide or carbon oxysulfide, base and alkylating agent to give the m-anilide-urethanes according to the invention.

The preferred synthesis steps are described in more detail below.

(a) The reaction of 3-nitrophenyl iso(thio)cyanates (B) is carried out with or without a catalyst usually used for iso(thio)cyanate reactions, e.g., tertiary amines (triethylamine, 1,4-diazabicyclo-(2,2,2)-octane), nitrogenous heterocyclic compounds (pyridine, 1,2-dimethylimidazole) or organic tin compounds (dibutyltin diacetate, dimethyltin dichloride), if desired in a solvent inert under the reaction conditions, e.g., hydrocarbons (ligroin gasoline, toluene, pentane, cyclohexane), halohydrocarbons (methylene chloride, chloroform, dichloroethane, chlorobenzene, o-, m- and p-dichlorobenzene), nitrohydrocarbons (nitrobenzene, nitromethane), nitriles (acetonitrile, butyronitrile, benzonitrile), ethers (diethyl ether, tetrahydrofuran, dioxane), esters (ethyl acetate, methyl propionate), ketones (acetone, methyl ethyl ketone), or amides (dimethylformamide, formamide)(German Laid-Open Application DE-OS No. 1,568,138), at from 0° to 150° C., preferably 40° to 100° C.

(b) 3-nitranilines (A) and 3-aminoanilides (H) are reacted with chloroformates in a suitable solvent, e.g., water, alcohols (methanol, ethanol, isopropanol), or as under (a), with the aid of a conventional acid binder, e.g., alkali metal hydroxides, carbonates and bicarbonates, alkaline earth metal oxides, hydroxides, carbonates and bicarbonates, or tertiary organic bases (e.g., triethylamine, pyridine, N,N-dimethylamine, N,N-dimethylcyclohexylamine, quinoline or tributylamine), or starting material 3-nitraniline, at from −20° to +150° C., preferably from +20° to 80° C.

(c) The nitrourethanes (C) and nitroanilides may be reduced by one of the conventional processes, e.g., by catalytic hydrogenation, with a metal/acid combination, e.g., a combination of iron and acid, or with a metal/alcohol combination, e.g., zinc dust and aqueous alcohol, or iron and aqueous alcohol.

(d) 3-Nitroanilines (A) and aminourethanes (D) are reacted with phenoxycarboxylic acid halides or with halocarboxylic acid halides in a suitable solvent, with the addition of a conventional acid binder as given under (a), at from −20° to +150° C., preferably from 0° to 60° C.

Instead of the acid halides, the acids themselves may also be used if they are activated with an aliphatic carbodiimide, e.g., dicyclohexylcarbodiimide. Particularly suitable solvents of those given under (a) e.g., tetrahydrofuran; the preferred temperature range is from 0° to 60° C.

The 3-nitranilines (A) and aminourethanes (D) are reacted with phenoxycarboxylic acid esters either without a solvent or in an indifferent solvent, such as hydrocarbons (toluene), halohydrocarbons (dichlorobenzene) or amides (dimethylformamide), at from 50° to 180° C., preferably from 80° to 150° C.

(e) The haloamide urethanes (E) and the nitrohaloamides (F) are reacted either with alkali metal (thio)phenolates in an indifferent solvent as under (a), or with finely pulverized potassium carbonate and (thio)phenol in a ketone (acetone, methyl ethyl ketone), at from 0° to 150° C., preferably from 40° to 100° C.

The following examples illustrate the preparation of the new m-anilide-urethanes and their precursors.

I. Nitrourethanes

EXAMPLE A

87 Parts by weight of sodium bicarbonate is added to 138 parts by weight of m-nitraniline in 500 parts by weight of tetrahydrofuran. While stirring, 120 parts by weight of thiomethyl chloroformate is dripped in at room temperature, the mixture is stirred for 16 hours at room temperature and then filtered, the solvent is distilled off in a rotary evaporator, and the oil which is obtained is stirred into toluene. The crystals which separate out are filtered and dried; m.p.: 137°–138° C.

The compound has the following structural formula:

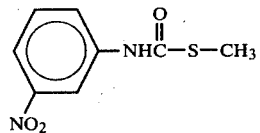

EXAMPLE B

51 Parts by weight of tert-butanol is added to 112 parts by weight of 3-nitrophenyl isocyanate in 600 parts by weight of toluene. A few drops of triethylamine are added after 4 hours, and the mixture is allowed to stand for 48 hours. White crystals are obtained after removal of the solvent in vacuo. Melting point: 97°–99° C.

The compound has the following structural formula:

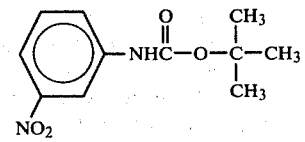

The following nitrourethanes (C) may be prepared analogously:

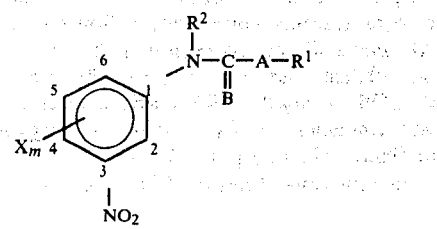

| A | B | X | R¹ | R² | m.p. °C. |
|---|---|---|---|---|---|
| O | O | H | CH₃ | H | 153–155 |
| O | S | H | CH₃ | H | |
| O | O | 6-CH₃ | CH₃ | H | 132–133 |
| O | O | H | phenyl | H | 123–125 |
| O | O | H | phenyl | CH₃ | 69–70 |
| O | O | 6-F | phenyl | H | 138–140 |
| O | O | 5-CF | CH₃ | H | 86–87 |
| O | O | 6-CH₃ | C₂H₅ | H | 131–133 |
| O | O | H | C₂H₅ | H | 64–66 |
| O | O | 2-CH₃ | phenyl | H | 112–114 |
| O | O | 4-CH₃ | CH₃ | H | 114–117 |
| O | O | H | cyclooctyl | H | 103–105 |
| O | O | H | CH₂COOCH₃ | H | 123–125 |
| O | O | 5-CF₃ | CH(CH₃)₂ | H | 121–123 |
| O | O | H | CH₃ | CH₃ | 58–61 |
| O | O | H | 3,5-dimethylcyclohexyl | H | 128–129 |
| O | O | H | CH(CH₃)₂ | H | 86–88 |
| O | O | 6F | CH₃ | H | 116–118 |
| O | O | 4Cl | phenyl | H | 125–127 |
| O | O | 4Cl | CH₃ | H | 122–124 |
| O | O | 4-CH₃ | C₂H₅ | H | 80–81 |
| O | O | H | 1-methylcyclopentyl | H | 57–59 |
| O | O | 5-CF₃ | phenyl | H | 133–135 |
| O | O | H | 2,6-dimethylcyclohexyl | H | 121–123 |
| O | O | 6OCH₃ | CH₃ | H | 134–136 |
| O | O | H | cycloheptyl | H | 102–104 |
| O | O | 6OCH₃ | phenyl | H | 209–211 |
| O | S | H | phenyl | H | |
| O | O | H | cyclopentyl | H | 110–112 |
| O | O | 6Cl | CH₃ | H | 136–138 |
| O | O | H | 3-methylcyclohexyl | H | 120–122 |
| S | S | H | CH₃ | H | |
| S | O | H | C(CH₃)₃ | H | |
| S | O | H | C₂H₅ | H | |
| S | O | H | phenyl | H | 156–158 |
| O | O | C₂H₅ | phenyl | H | 56–58 |
| O | O | H | C(CH₃)₂C₂H₅ | H | 62–63 |
| O | O | H | CH(CH₂OCH₃)₂ | H | 95–96 |
| O | O | H | cyclohexyl | H | 117–118 |

II. Aminourethanes
EXAMPLE C

While stirring vigorously, 40 parts by weight of 3-(S-methylthiocarbamoyl)-nitrobenzene is added to a mixture, heated at 80° C., of 33 parts by weight of iron powder, 75 parts by weight of alcohol, 60 parts by weight of water and 3 parts by weight of concentrated hydrochloric acid in such portions that the temperature is kept at 80° C. without additional heating. The mixture is then refluxed for 1 hour and filtered hot, the residue and the filtrate are digested with about 1,000 parts by weight of methylene chloride, followed by drying over sodium sulfate, concentration and recrystallization from toluene; m.p.: 101°–103° C.

Structure:

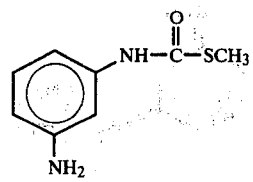

The following aminourethanes (D) may be prepared analogously:

| A | B | X | R¹ | R² | m.p. °C. |
|---|---|---|---|---|---|
| O | O | H | CH₃ | H | 87–89 |
| O | O | 6CH₃ | CH₃ | H | |
| O | O | H | phenyl | CH₃ | 70–72 |
| O | O | 4F | CH₃ | H | |
| O | S | H | CH₃ | H | |
| S | O | H | C₂H₅ | H | |
| O | S | H | phenyl | H | |
| O | O | 5CF₃ | CH₃ | H | viscous oil |
| O | O | H | C₂H₅ | H | viscous oil |
| O | O | 2CH₃ | phenyl | H | 131–133 |
| O | O | 4CH₃ | CH₃ | H | |
| O | O | 4Cl | phenyl | H | 215–217 |
| O | O | 4Cl | CH₃ | H | |
| O | O | 4CH₃ | C₂H₅ | H | |
| S | S | H | phenyl | H | |
| O | O | H | 3,3,5-trimethylcyclohexyl | H | 100–102 |
| O | O | H | phenyl | C₂H₅ | 104–106 |
| O | O | H | cyclopentyl | H | |
| O | O | 5-CF₃ | phenyl | H | 214–216 |
| O | O | H | phenyl | H | 178–180 |
| O | O | H | 1-methylcyclopentyl | H | |
| O | O | H | hexahydrobenzyl | H | 106–108 |
| O | O | 6OCH₃ | CH₃ | H | 85–87 |
| O | O | H | cycloheptyl | H | 86–88 |
| O | O | 6OCH₃ | phenyl | H | 84–86 |
| O | O | 6Cl | CH₃ | H | |
| O | O | H | 3-methylcyclohexyl | H | 95–97 |
| O | O | H | CH₂COOCH₃ | H | viscous oil |
| S | S | H | CH₃ | H | |
| O | O | H | C(CH₃)₃ | H | 109–110 |
| O | O | 5-CF₃ | CH(CH₃)₂ | H | 102–104 |
| O | O | H | CH₃ | CH₃ | 89–92 |
| O | O | H | 3,5-dimethylcyclohexyl | H | 80–82 |
| O | O | H | CH(CH₃)₂ | H | 66–68 |
| O | O | 4F | CH₃ | H | |
| O | O | H | C(CH₃)₂C₂H₅ | H | 65–67 |
| O | O | H | cyclohexyl | H | 122–124 |

III. Nitrohaloamides and haloamide urethanes

EXAMPLE D 126 parts by weight of sodium bicarbonate is added to 138 parts by weight of 3-nitroaniline in 1,500 parts by weight of ethyl acetate. At 0° to 10° C. and while stirring, 216 parts by weight of 2-bromopropionyl bromide is dripped in, the mixture is then stirred for 16 hours at room temperature, filtered and concentrated, and the crystals which are obtained are washed with toluene; m.p.: 99°–101° C.

The compound has the following structural formula (cf. F):

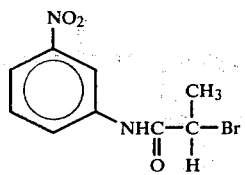

The following haloamide urethanes (E) may be prepared analogously:

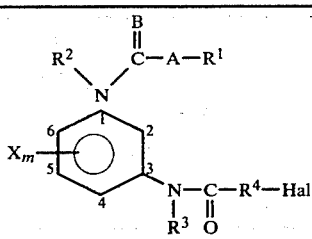

| A | B | X | R² | R¹ | R³ | R⁴ | Hal | m.p. °C. |
|---|---|---|----|----|----|----|-----|----------|
| O | O | H | H | methyl | H | —CH(CH₃)— | Cl | 138–141 |
| O | O | H | H | methyl | H | —CH₂— | Cl | 168–170 |
| S | S | H | H | methyl | H | —CH(CH₃)— | Cl | |
| O | O | H | H | methyl | H | —C(CH₃)₂—CH₂— | Cl | 125–127 |
| O | O | H | H | methyl | H | —CH(C₂H₅)— | Br | 131–133 |
| O | O | H | H | ethyl | H | —CH₂— | Cl | |
| O | O | H | H | methyl | H | —C(CH₃)₂— | Br | 91–93 |
| O | O | 4CH₃ | H | methyl | H | —CH(CH₃)— | Br | 207–210 |
| O | O | H | H | methyl | H | —(CH₂)₃— | Cl | |
| S | O | H | H | methyl | H | —CH(CH₃)— | Br | 160–162 |
| O | O | H | H | methyl | H | —CH(CH₃)— | Br | 142–143 |
| O | S | H | H | methyl | H | —CH(CH₃)— | Br | |
| O | O | H | H | phenyl | H | —CH₂— | Cl | 170–173 |
| O | O | H | CH₃ | methyl | H | —CH(CH₃)— | Cl | |
| O | O | H | H | phenyl | H | —C(CH₃)₂—CH₂— | Cl | 143–145 |
| O | O | H | H | phenyl | H | —CH(CH₃)— | Cl | 170–172 |
| O | O | H | H | methyl | CH₃ | —CH(CH₃)— | Br | |

IV. 3-Nitro- and 3-aminoanilides

EXAMPLE E

At room temperature and while stirring well, 254 parts by weight of α-(2,4-dichlorophenoxy)-propionyl chloride is dripped into a mixture of 152 parts of N-methyl-3-nitroaniline, 126 parts by weight of sodium bicarbonate and 800 parts by weight of ethyl acetate. The mixture is stirred for 16 hours at room temperature and then filtered, the solvent is distilled off in a rotary evaporator, and the residue is stirred with petroleum ether, filtered and dried; m.p.: 125°–127° C.

The compound has the following structural formula:

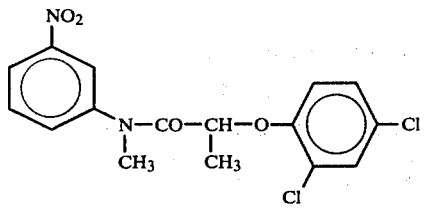

EXAMPLE F 62 parts by weight of 3-nitroaniline and 96.5 parts by weight of α-(2-methyl-4-chlorophenoxy)-propionic acid are dissolved in 300 parts by weight of tetrahydrofuran. While stirring and at room temperature, 102 parts by weight of dicyclohexylcarbodiimide in 200 parts by weight of tetrahydrofuran is slowly added. After the mixture has been stirred for 16 hours it is filtered and concentrated, and the residue is dissolved in ethyl acetate, shaken with 5% strength sodium hydroxide solution, 5% strength hydrochloric acid and water, dried and concentrated. The residue is recrystallized from methanol. Melting point: 124°–127° C.

The compound has the following structural formula:

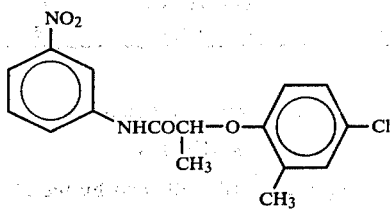

EXAMPLE G

A mixture of 219 parts by weight of α-(2,4-dichlorophenoxy)-propionic acid-m-nitroanilide, 7 parts by weight of 10% palladium on animal charcoal and 2,000 parts by weight of tetrahydrofuran is hydrogenated at room temperature and atmospheric pressure. After the theoretical hydrogen absorption, the mixture is filtered, freed from solvent and crystallized with petroleum ether. Melting point: 125°–128° C.

The compound has the following structural formula:

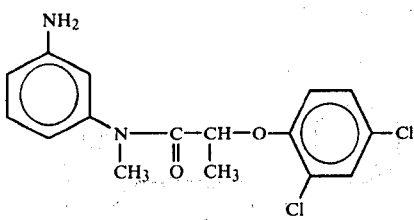

The following 3-nitroanilides (G) and 3-aminoanilides (H) may be prepared analogously:

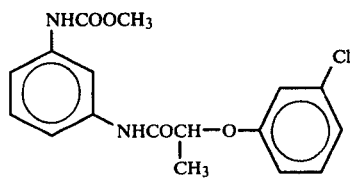

| Z | X | $R^3$ | $R^4$ | D | Y | m.p. °C. |
|---|---|---|---|---|---|---|
| $NO_2$ | H | H | —CH(CH$_3$)— | O | 2,4-Cl$_2$ | 164–166 |
| $NO_2$ | H | H | —CH$_2$— | O | 2,4-Cl$_2$ | 203–205 |
| $NO_2$ | 4F | H | —CH(CH$_3$)— | O | 2CH$_3$4Cl | |
| $NO_2$ | H | CH$_3$ | —CH(CH$_3$)— | O | 2,4,5Cl$_3$ | |
| $NO_2$ | H | H | —(CH$_2$)$_3$— | O | 2,4Cl$_2$ | |
| $NO_2$ | H | H | —CH(CH$_3$)— | S | H | |
| $NO_2$ | H | H | —CH(CH$_3$)— | O | 2,4(CH$_3$)$_2$ | |
| $NO_2$ | H | H | —CH(CH$_3$)— | O | 3Cl | |
| $NO_2$ | 6OCH$_3$ | H | —CH(CH$_3$)— | O | 2,4-Cl$_2$ | 185–187 |
| $NH_2$ | H | H | —CH(CH$_3$)— | O | 2,4Cl$_2$ | 131–134 |
| $NH_2$ | H | H | —CH(CH$_3$)— | O | 2CH$_3$—4Cl | 82–84 |
| $NH_2$ | H | H | —CH$_2$— | O | 2,4Cl$_2$ | 125–127 |
| $NH_2$ | 4F | H | —CH(CH$_3$)— | O | 2CH$_3$—4Cl | |
| $NH_2$ | H | CH$_3$ | —CH(CH$_3$)— | O | 2,4,5Cl$_3$ | |
| $NH_2$ | H H | —CH(CH$_2$)$_3$)— | | O | 2,4Cl$_2$ | |
| $NH_2$ | H | H | —CH(CH$_3$)— | S | H | |
| $NH_2$ | H | H | —CH(CH$_3$)— | O | 2,4(CH$_3$) | |
| $NH_2$ | H | H | —CH(CH$_3$)— | O | 3Cl | |

V. m-Anilide-urethanes

EXAMPLE 1

21.1 Parts by weight of methyl α-(3-chlorophenoxy)-propionate and 16.3 parts by weight of 3-(O-methoxycarbamoyl)-aniline are kept at 130° C. for 48 hours. The crude product is chromatographed on silica gel using a mixture of 95 parts of methylene chloride and 5 parts of methanol. White crystals are obtained which melt at 129°–131° C. and have the following structural formula:

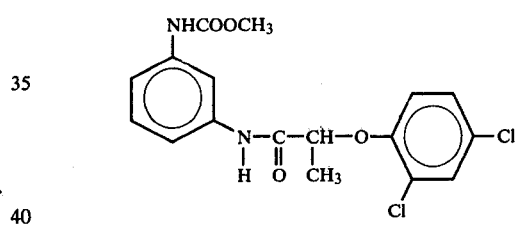

EXAMPLE 2

At room temperature, 3.8 parts by weight of thiomethyl chloroformate is dripped into a mixture of 10.5 parts by weight of α-(2-methyl-4-chlorophenoxy)-propionic acid-(m-aminoanilide), 6 parts by weight of sodium bicarbonate and 150 parts by weight of tetrahydrofuran. After the mixture has been stirred for 10 hours, it is filtered and concentrated. The oil which is obtained is crystallized with toluene/petroleum ether. Melting point: 148°–150° C.

The compound has the following structural formula:

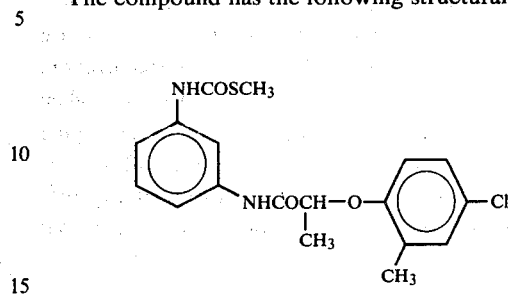

EXAMPLE 3

At room temperature and while stirring well, 24.8 parts by weight of α-(2,4-dichlorophenoxy)-propionyl chloride is dripped into a mixture of 11.6 parts by weight of 3-(O-methylcarbamoxyl)-aniline, 10.5 parts by weight of sodium bicarbonate and 200 parts by weight of tetrahydrofuran. The mixture is stirred for 16 hours at room temperature and then filtered, the solvent is distilled off in a rotary evaporator and the residue is recrystallized from diethyl ether. Melting point: 108°–110° C.

The compound has the following structural formula:

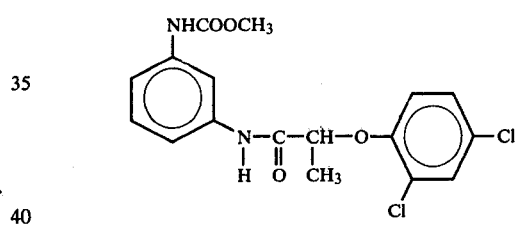

EXAMPLE 4

157 Parts by weight of 3-(O-methylcarbamoyl)-aniline and 200 parts by weight of α-(2-methyl-4-chlorophenoxy)-propionic acid are dissolved in 600 parts by weight of tetrahydrofuran. While stirring and at room temperature, 191 parts by weight of dicyclohexylcarbodiimide in 500 parts by weight of tetrahydrofuran is slowly added. After 3 hours the mixture is filtered and concentrated, and the residue is dissolved in ethyl acetate, shaken with 5% strength (by weight) sodium hydroxide solution, 5% strength hydrochloric acid and water, dried and concentrated. The residue is recrystallized from methanol. Melting point: 114°–115° C.

The compound has the following structural formula:

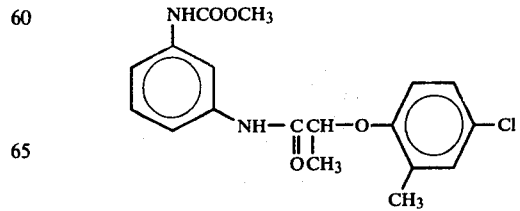

EXAMPLE 5

25.7 Parts by weight of α-chloropropionic acid-3-(O-methylcarbamoyl)-anilide, 22.7 g of sodium-4-chlorophenolate and 200 parts by weight of acetonitrile are boiled for 14 hours. After filtration and concentration, the residue is taken up in methylene chloride and shaken with dilute sodium hydroxide solution. After drying over sodium sulfate, the solvent is distilled off and the residue is chromatographed on silica gel using methylene chloride. White crystals are obtained which melt at from 148° to 151° C. The compound has the following structural formula:

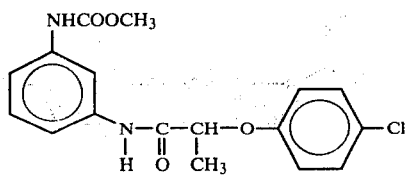

The following compounds may be prepared analogously:

| NO. | A | B | D | R¹ | R² | R³ | R⁴ | X | Y | m.p. °C. |
|---|---|---|---|---|---|---|---|---|---|---|
| 6 | O | O | O | C₂H₅ | H | H | —CH(CH₃)— | H | 2,4Cl₂ | 83–85 |
| 7 | O | O | O | CH₃ | CH₃ | H | —CH(CH₃)— | H | 2,4Cl₂ | 120–122 |
| 8 | O | O | O | CH₃ | H | CH₃ | —CH(CH₃)— | H | 2,4Cl₂ | 161–163 |
| 9 | O | S | S | t-C₄H₉ | H | H | —CH(CH₃)— | H | 2,4Cl₂ | 119–121 |
| 10 | O | O | O | CH₂CH₂OCH₃ | H | H | —(CH₂)₂ | 5-CH₃ | 4N(CH₃)₂ | |
| 11 | O | O | O | C₂H₅ | C₂H₅ | H | —C(C₂H₅)(CH₂Cl)—CH₂— | H | 4-SCH₃ | 84–85 |
| 12 | O | S | O | CH₂CN | H | H | —CH(CH₃)— | H | 2,4Cl₂ | |
| 13 | O | O | O | CH₃ | iC₃H₇ | H | —CH(CH₃)— | H | 3SO₂CH₃ | 142–144 |
| 14 | O | O | O | CH₃ | H | H | —CH(iC₃H₇)— | H | 4Cl | 137–139 |
| 15 | O | O | O | CH₃ | CH₂OCH₃ | H | —CH(CH₃)— | H | 2,4Cl₂ | 179–181 |
| 16 | O | O | O | CH₃ | H | H | —CH(CH₃)— | H | 4OCF₂CHF₂ | |
| 17 | O | O | O | CH₃ | H | C₂H₅ | —CH(CH₃)— | H | 2,4,5Cl₃ | 152–154 |
| 18 | S | S | S | i-C₃H₇ | CH₂CH₂OCH₃ | H | —CH₂— | H | 3CH₂OCH₃ | |
| 19 | O | O | O | C₂H₅ | 3H | H | —CH(CH₃)— | H | 2,4Cl₂ | |
| 20 | O | O | O | CH₃ | H | —CH(CH₃)— | H | H | 4 cyclohexyl | |
| 21 | O | O | O | CH₃ | H | i-C₃H₇ | H | 3-NHCOCH₃ | 2,4Cl₂ | 111–113 |
| 22 | O | O | O | CH₂C≡CH | H | CH₃ | —CH₂— | H | 2,4,J₂ | |
| 23 | O | O | O | CH₃ | CH₂Cl | H | —CH(CH₃)— | H | 2,4Cl₂ | 101–103 |
| 24 | O | O | S | CH₃ | H | H | —CH(C₂H₅)— | H | 2,4Cl₂ | 124–126 |
| 25 | O | O | O | CH₃ | H | H | CH(CH₂OCH₃)— | H | 2,4Cl₂ | |
| 26 | O | S | O | CH₃ | H | H | —CH(CH₃)— | H | 2,4Cl₂ | viscous oil |
| 27 | O | O | S | CH₃ | H | H | —CH(CH₃)— | H | 2,4Cl₂ | 147–148 |
| 28 | O | O | O | CH₂CH₂OCH₃ | H | H | —CH(CH₃)— | H | 2,4Cl₂ | |
| 29 | O | O | O | CH₃ | H | H | —C(CH₃)₂ | H | 2,4Cl₂ | |
| 30 | O | O | O | CH₃ | H | H | —CH(CH₂Cl)— | H | 2Cl₃,4Cl | |
| 31 | O | S | O | CH₂CH₂Cl | H | H | —CH(CH₃)— | H | 2,4Cl₂ | |
| 32 | O | O | O | C₂H₅ | H | H | —CH(CH₃)— | H | 3 SCN | 59–61 |
| 33 | O | O | O | CH₃ | CH₃ | H | —CH(CH₂CH₂OCH₃)—CH₂— | 4CH₃ | 2CH₃,4Cl | |
| 34 | O | O | O | CH₂COOCH₃ | H | H | —C(CH₃)(C₂H₅)— | H | 2,4Cl₂ | 146–148 |
| 35 | O | O | O | CH₃ | H | H | —(CH₂)₃— | H | 2,4Cl₂ | 110–112 |
| 36 | O | S | S | CH₂C≡CH | H | H | —CH(CH₂CH₂OCH₃) | 6Cl | 3-COOCH₃ | 76–78 |
| 37 | O | O | O | CH₂CH=CH₂ | H | H | —CH(CH₃)— | H | 2,4Cl₂ | |
| 38 | O | O | O | CH₃ | CH₃ | H | —C(C₂H₅)₂— | H | 2Br,4Cl | 189–190 |
| 39 | O | O | O | CH₃ | H | H | —CH₂— | H | 2,4Cl₂ | 88–89 |
| 40 | S | O | O | CH₃ | H | H | —CH(CH₃)— | H | 2,4Cl₂ | |
| 41 | O | O | O | t-C₄H₉ | H | H | —C(CH₃)(CH₂Cl)— | H | 2CH₃,4Cl | |
| 42 | O | O | O | CH₃ | H | H | —(CH₂)₂— | H | 2,4,5Cl₃ | |
| 43 | O | O | O | CH₃ | H | H | —(CH₂)₂— | H | | |

-continued

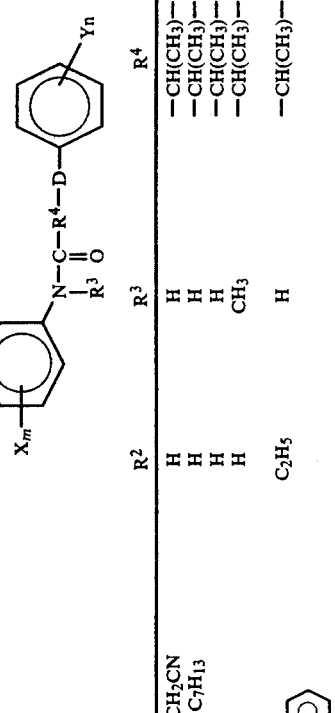

| NO. | A | B | D | R¹ | R² | R³ | R⁴ | X | Y | m.p. °C. |
|---|---|---|---|---|---|---|---|---|---|---|
| 44 | S | O | O | CH₂CH₂CN | H | H | —CH(CH₃)— | H | 2F 4Br | 82–84 |
| 45 | O | O | O | cycl. C₇H₁₃ | H | H | —CH(CH₃)— | H | 2,4Cl₂ | 188–190 |
| 46 | O | O | O | CH₃ | H | H | —CH(CH₃)— | 6-Cl | 2,4Cl₂ | |
| 47 | S | O | O | CH₃ | H | CH₃ | —CH(CH₃)— | H | 2,4Cl₂ | 97–98 |
| 48 | O | O | O | ⌬ | C₂H₅ | H | —CH(CH₃)— | H | 2,4Cl₂ | |
| 49 | O | O | O | CH(CH₃)CH₂CN | H | H | —CH(CH₃)— | H | 3-NHCON(CH₃)₂ | |
| 50 | O | O | O | CH₃ | H | H | —CH(CH₃)— | H | 2Cl 4Br | 122–124 |
| 51 | O | O | O | CH₃ | H | H | —CH₂— | H | H | 155–156 |
| 52 | O | O | O | CH₃ | H | H | —CH(CH₃)— | H | 2Br 4Cl | 145–147 |
| 53 | O | O | O | CH₃ | H | H | —CH(CH₃)— | H | 4F | 110–111 |
| 54 | O | O | O | CH(CH₃)CN | H | H | —CH(nC₃H₇)— | H | 3 CONHCH₃ | |
| 55 | O | O | O | C₂H₅ | H | CH₃ | —CH(CH₃)— | H | 2,4Cl₂ | 150–153 |
| 56 | O | O | O | i-C₄H₉ | H | H | —CH(CH₃)— | H | 2Br 4Cl | 138–140 |
| 57 | O | O | O | CH₃ | H | H | —CH(CH₃)— | H | 2Cl | 153–155 |
| 58 | O | O | O | CH₃ | H | H | —CH(CH₃)— | H | 4Br | |
| 59 | O | O | O | CH₂—CCl=CH₂ | H | H | —CH(CH₃)—(CH₂)₃— | 2CH₃ | 4NHCONHCH₃ | |
| 60 | O | O | O | CH₃ | H | H | —CH₂— | H | 3,4Cl₂ | 185–187 |
| 61 | O | O | O | CH₃ | H | H | —CH(CH₃)— | H | 3CF₃ | 97–99 |
| 62 | O | O | O | CH(CH₃)CH=CH₂ | H | H | —CH(CH₃)— | H | 2,4Cl₂ | |
| 63 | O | O | S | CH₂C≡CCH₂Cl | H | H | —CH(CH₃)— | H | 4OSO₂CH₃ | |
| 64 | O | O | O | CH₃ | H | H | —(CH₂)₄— | H | 2,4,5Cl₃ | 120–122 |
| 65 | O | O | O | CH₃ | H | H | —CH(CH₃)— | H | 2Cl4F | 141–143 |
| 66 | O | O | O | CH₃ | H | H | —CH(CH₃)— | 6-OCH₃ | 2,4Cl₂ | |
| 67 | O | O | O | CH₃ | H | H | —CH(CH₃)— | H | ⌬ | viscous oil |
| 68 | O | O | O | CH₂C≡CCH₂OCH₃ | H | H | —CH(nC₄H₉)— | H | 2-COCH₃ | |
| 69 | S | O | O | nC₃H₇ | H | H | —(CH₂)₅— | H | 4SO₂NHCH₃ | |
| 70 | O | O | O | CH₃ | H | H | —CH(CH₃)— | H | 3CH₃ 4Cl | 136–137 |
| 71 | O | O | O | CH₃ | H | H | —CH(CH₃)— | H | 2,4(CH₃)₂ | 110–112 |
| 72 | O | O | O | CH(CH₃)C≡CH | H | H | —CH(CH₃)— | H | 2Br 4Cl | |
| 73 | O | O | O | CH₃ | H | H | —CH(CH₃)—CH₂— | H | 2,4Cl | |
| 74 | S | O | O | tert. C₄H₉ | H | CH₃ | —CH(CH₃)— | H | 2,4Cl | 149–151 |

-continued

| NO. | A | B | D | R¹ | R² | R³ | R⁴ | X | Y | m.p. °C. |
|---|---|---|---|---|---|---|---|---|---|---|
| 75 | O | O | O | cycl. C₅H₉ | H | H | —CH(CH₃)— | H | 2,4Cl₂ | 164-166 |
| 76 | O | O | O | CH₃ | H | H | —C(CH₃)₂—CH₂— | H | 2,4Cl₂ | |
| 77 | O | O | O | CH₃ | H | H | —CH(CH₃)— | 4CH₃ | 2,4Cl₂ | 131-134 |
| 78 | O | O | O | cycl. C₆H₁₁ | H | H | —CH(CH₃)— | H | 2,4,5Cl₃ | |
| 79 | O | O | O | CH₃ | H | H | —CH(CH₃)—(CH₂)₂— | H | 2,4Cl₂ | |
| 80 | O | O | O | CH₃ | H | H | —CH(CH₃)— | H | 2,3Cl₂ | |
| 81 | O | O | O | CH₃ | H | H | —CH(CH₃)— | 2-CH₃ | 2,4Cl₂ | 113-115 |
| 82 | O | O | O | CH₃ | H | H | —CH(CH₃)— | H | 2-CH₂—⌬,4Cl | |
| 83 | O | O | O | sec. C₄H₉ | H | H | —C(CH₃)₂— | H | 2,4,5Cl₃ | 146-148 |
| 84 | O | O | O | tert. C₅H₁₁ | H | H | —CH(CH₃)— | H | 2CH₃4Cl | |
| 85 | O | O | O | CH₃ | H | H | —CH(CH₃)— | H | 2,4,6Cl₃ | 138-140 |
| 86 | O | O | O | ⌬ | H | H | —CH(CH₃)— | H | 2,4Cl₂ | |
| 87 | S | S | O | CH₃ | H | H | —CH(CH₃)—(CH₂)₄— | H | 2,4,5Cl₃ | 162-164 |
| 88 | O | O | S | CH₂CH₂F | H | H | —CH₂— | H | 4-Cl | 63-64 |
| 89 | O | O | O | CH₃ | H | H | —CH(CH₃)— | H | 2,4,5Cl₃ | |
| 90 | O | O | O | CH₂CF₃ | H | H | —CH(CH₃)— | H | 3,5Cl₂ | |
| 91 | O | O | O | CH₃ | H | H | —CH(CH₃)— | H | 2-SO₂N(CH₃)₂ | |
| 92 | O | O | O | CH₂CH₂OCH₃ | H | H | —CH(CH₃)—(CH₂)₄— | H | 2,4Br₂ | |
| 93 | O | O | S | CH₂CH₂OCH₃ | H | H | —C(CH₃)₂—(CH₂)₄— | H | 2Br 4Cl | 65-68 |
| 94 | O | O | O | CH₃ | CH₃ | H | —CH(CH₃)— | H | 2,5Cl₂ | |
| 95 | O | O | S | CH(CH₃)CH₂OCH₃ | H | CH₃ | —C(CH₃)(C₂H₅)(CH₂)₂— | H | 4 F | 110-113 |
| 96 | O | O | O | CH₃ | H | CH₃ | —CH(C₃H₇)— | H | 4OCH₃ | viscous oil |
| 97 | O | O | O | CH(CH₃)COOC₂H₅ | H | H | —CH(CH₃)— | H | 2,4Cl₂ | 150-152 |
| 98 | O | O | O | CH₃ | H | CH₃ | —CH(CH₃)— | H | 4NO₂ | 105-107 |
| 99 | O | O | O | CH₂CH₂OCH₃ | H | H | —CH(CH₃)— | 5-CH₃ | 3 OCH₃ | |
| 100 | O | O | O | CH₂CH₂COOCH₃ | H | H | —CH(CH₃)—(CH₂)₅— | H | H | |
| 101 | O | O | O | CH₃ | H | H | —CH(CH₃)— | H | 4 OCH₃ | 112-114 |
| 102 | O | O | O | CH₃ | H | H | —CH(CH₃)— | H | 3 NO₂ | 60-62 |
| 103 | O | O | O | cycl. C₇H₁₃ | H | H | —CH(CH₃)— | H | 3NHCOOCH₃ | |
| 104 | S | O | O | CH₃ | H | H | —CH(CH₃)—(CH₂)₅— | H | 2CH₃4Cl | |

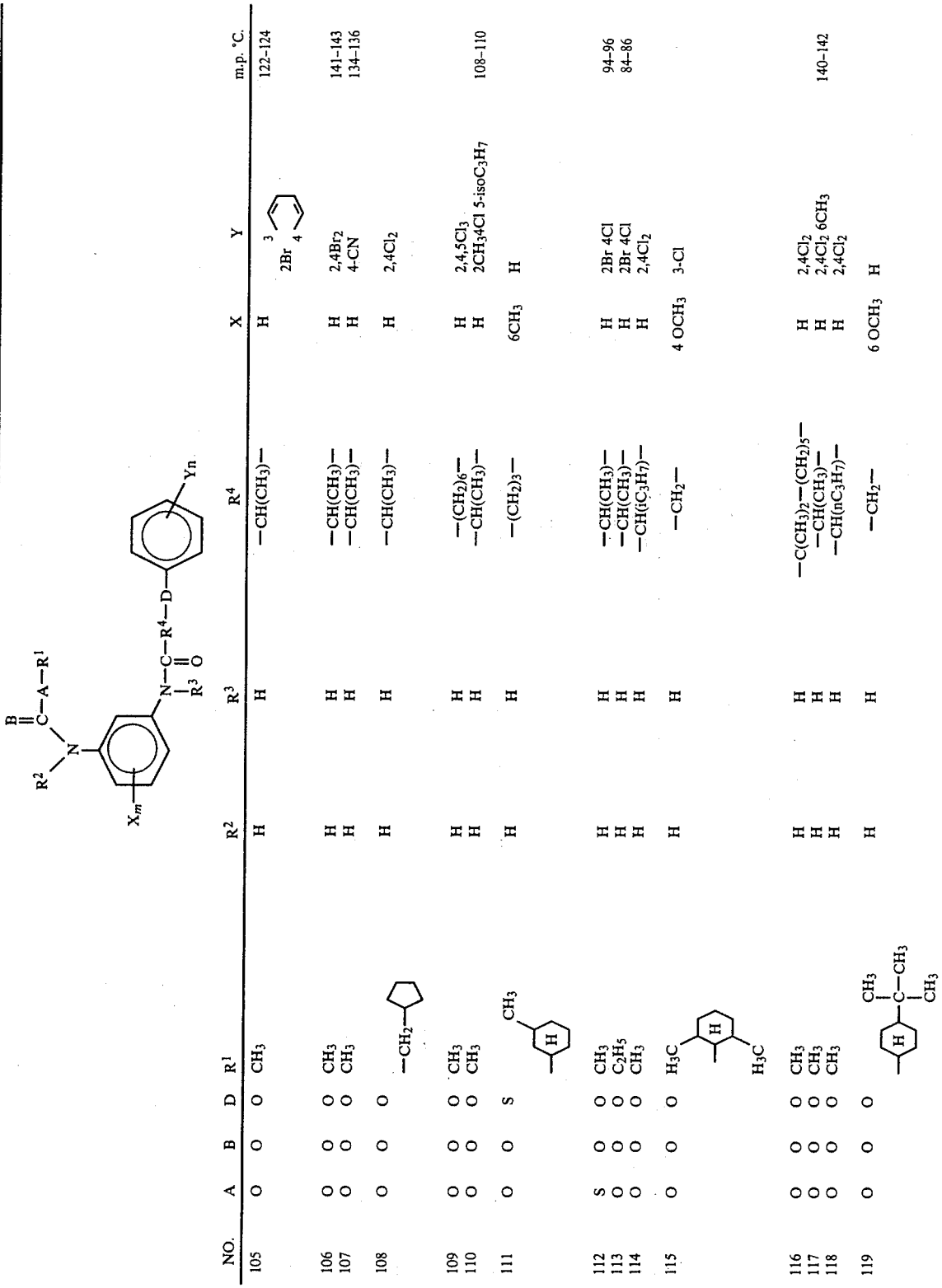

-continued

| NO. | A | B | D | R¹ | R² | R³ | R⁴ | X | Y | m.p. °C. |
|---|---|---|---|---|---|---|---|---|---|---|
| 120 | O | O | O | CH₃ | H | H | —CH(CH₃)— | H | 2Br 4F | 130-132 |
| 121 | O | O | O | ⌬ | CH₂CH₂Cl | H | —(CH₂)₃— | 4 Cl | H | |
| 122 | O | O | O | C₂H₅ | H | H | —C(CH₃)(CH₂CH₂Cl)—(CH₂)₂— | H | 4 Br | |
| 123 | S | S | O | CH₃ | H | CH₂CH₂OCH₃ | —CH₂— | 5 CF₃ | 3 CF₃ | |
| 124 | O | O | O | CH₃ | H | H | —C(CH₃)₂—(CH₂)₂— | H | 2,4Cl₂ | |
| 125 | O | O | O | H₃C–⌬ | H | H | —CH(CH₃)— | H | 2,4 Cl₂ | 96-98 |
| 126 | O | O | O | CH₃ | H | H | —CH(CH₃)— | H | 2COOCH₃4Cl | 153-155 |
| 127 | S | S | O | CH₃ | H | H | —CH(CH₃)—(CH₂)₃— | H | 4 F | 145-148 |
| 128 | O | O | O | i-C₃H₇ | H | H | —CH(CH₃)— | H | 2CH₃4Cl | |
| 129 | O | O | O | CH₃ | H | H | —(CH₂)₄— | H | 2,4 Cl₂ | |
| 130 | O | O | O | CH₃ | H | H | —C(CH₃)₂—CH₂— | H | 2CH₃4Cl | 103-105 |
| 131 | O | O | O | CH₃ | H | CH₂Cl | —CH(CH₃)— | H | 2 F | |
| 132 | S | O | O | CH₃ | H | H | —CH(CH₃)— | H | 2Br 4Cl | 173-175 |
| 133 | O | O | O | C₃ | H | H | —CH₂— | H | 2CH₃ 4Cl | |
| 134 | O | O | O | CH₃ | H | H | —C(CH₃)(CH₂OCH₃)— | H | 2,4 Cl₂ | 98-100 |
| 135 | O | O | O | CH₃ | H | H | —CH(CH₃)— | H | 2Cl4NO₂ | |
| 136 | O | O | O | CH₃ | H | H | —CH(CH₃)— | H | 3 F | |
| 137 | O | O | O | CH₃ | H | H | —CH(CH₃)— | H | 2Br 4NO₂ | |
| 138 | S | S | O | CH₃ | H | H | —C(CH₃)₂—(CH₂)₃— | H | 2,4,5-Cl₃ | |
| 139 | O | O | O | CH₃ | H | H | —(CH₂)₆— | H | 2,4 Cl₂ | 199-202 |
| 140 | O | O | O | CH₃ | H | H | —CH(CH₃)— | H | 2NO₂ 4Cl | 112-114 |
| 141 | O | O | O | CH₃ | H | H | —CH(CH₃)— | H | 2Br 4SCH₃ | 170-172 |
| 142 | S | O | O | CH₃ | H | H | —CH(CH₃)— | H | 2,4Cl₂ | |
| 143 | O | O | O | CH₃ | H | H | —CH(CH₃)— | H | 2CHO 4Cl | |
| 144 | O | O | O | CH₃ | H | H | —CH(CH₃)— | H | 2Br 4 OCH₃ | |
| 145 | O | O | O | CH₃ | H | H | —CH(CH₃)— | 4Cl | 2,4 Cl₂ | 133-135 |
| 146 | O | O | O | CH₃ | H | H | —CH(CH₃)— | H | 2Cl-5 OCH₃ | |
| 147 | O | O | O | CH₃ | H | H | —CH(CH₃)— | H | 2Cl-4 SCH₃ | 66-69 |
| 148 | O | O | S | CH₃ | H | H | —CH(CH₃)— | H | 2,4 Cl₂ | 143-144 |
| 149 | O | O | O | CH₃ | H | H | —CH₂— | H | 4 Cl | |

-continued

| NO. | A | B | D | R¹ | R² | R³ | R⁴ | X | Y | m.p. °C. |
|---|---|---|---|---|---|---|---|---|---|---|
| 150 | O | O | O | C₂H₅ | H | H | —CH(CH₃)— | H | 2CH₃4Cl | 112–114 |
| 151 | O | O | O | CH₃ | H | H | —CH(CH₃)— | H | 2Cl4SO₂CH₃ | 106–108 |
| 152 | O | O | O | CH₃ | H | H | —CH(CH₃)— | H | 3,4 Cl₂ | |
| 153 | O | O | O | CH₃ | H | H | —CH(CH₃)— | 4OCH₃ | 2,4 Cl₂ | |
| 154 | O | O | O | CH₃ | H | H | —CH(CH₃)— | H | 2F5C(CH₃)₃ | 115–117 |
| 155 | O | O | O | CH₃ | H | H | —CH(CH₃)— | H | 2,6 Cl₂ | 113–116 |
| 156 | O | O | O | CH₃ | H | H | —CH(CH₃)— | H | 2,4Cl₂ 6F | 114–115 |
| 157 | O | O | O | CH₃ | H | H | —CH(CH₃)— | H | H | 116–118 |
| 158 | O | O | O | CH₃ | H | H | —CH(CH₃)— | H | 2CN | 167–169 |
| 159 | O | O | O | CH₃ | H | H | —CH(CH₃)— | H | 3CN | 106–108 |
| 160 | O | O | O | CH₃ | H | H | —CH(CH₃)— | 6CH₃ | 3CH₃ | 162–164 |
| 161 | O | O | O | CH₃ | H | H | —CH(CH₃)— | H | 2,4 Cl₂ | |
| 162 | O | O | O | CH₃ | H | H | —(CH₂)₂— | H | 3C(CH₃)₃ | |
| 163 | O | O | O | CH₃ | H | H | —CH(CH₃)— | H | 2CH₂OCH₃4Cl | |
| 164 | O | O | O | CH₃ | H | H | —CH(CH₃)— | H | | |
| 165 | O | O | O | CH₃ | H | H | —CH(CH₃)— | H | | 155–157 |
| 166 | O | O | O | CH₃ | H | H | —CH(CH₃)— | 4CH₃ | 2Br4Cl | 123–125 |
| 167 | O | S | O | CH₃ | H | H | —CH(CH₃)— | H | 2,4 Cl₂ | 168–169 |
| 168 | O | O | O | CH₃ | H | H | —CH₂— | H | 2Br 4Cl | 190–192 |
| 169 | O | O | O | CH₃ | H | H | —CH(CH₃)— | H | 3Cl4F | |
| 170 | O | O | O | CH₃ | H | H | —(CH₂)₂CH(CH₃)— | H | 2,4 Cl₂ | |
| 171 | O | O | O | CH₃ | H | H | —C(CH₃)(CH₂)— | H | 2,4 Cl₂ | |
| 172 | O | O | O | CH₃ | H | H | —CH(CH₃)— | H | 2Cl5CH₃ | 104–106 |
| 173 | O | O | S | CH₃ | H | H | —CH(CH₃)— | H | 2,4 Cl₂ | 114–116 |
| 174 | O | O | O | CH₃ | H | H | —CH₂— | 5-CF₃ | H | 105–106 |
| 175 | O | O | O | CH₃ | H | H | —CH(CH₃)— | H | 2Br5C(CH₃)₃ | |
| 176 | O | O | O | CH₃ | H | H | —CH(CH₃)— | H | 2CH₃ 4,5Cl₂ | |
| 177 | O | O | O | CH₃ | H | H | —CH(CH₃)— | H | 2,4Cl₂5CH₃ | |
| 178 | O | O | O | CH₃ | H | H | —CH(CH₃)— | H | 2 Br | 89–91 |
| 179 | O | O | O | CH₃ | H | H | —CH(CH₃)— | H | 3 Br | 127–128 |
| 180 | O | O | O | CH₃ | H | H | —CH(CH₃)— | H | 2I | |
| 181 | O | O | O | CH₃ | H | H | —CH(CH₃)— | H | 3I | |
| 182 | O | O | O | CH₃ | H | H | —CH(CH₃)— | H | 4I | |
| 183 | O | O | O | CH₃ | H | H | —CH(CH₃)— | H | 2SCN | |
| 184 | O | O | O | CH₃ | H | H | —CH(CH₃)— | H | 3SCN | |

-continued

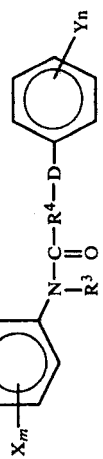

| NO. | A | B | D | R¹ | R² | R³ | R⁴ | X | Y | m.p. °C |
|---|---|---|---|---|---|---|---|---|---|---|
| 185 | O | O | O | CH₃ | H | H | —CH(CH₃)— | H | 4SCN | |
| 186 | O | O | O | CH₃ | H | H | —CH(CH₃)— | H | 2,4F₂ | 119–122 |
| 187 | O | O | O | CH₃ | H | H | —CH(CH₃)— | H | 2F4Cl | |
| 188 | O | O | O | CH₃ | H | H | —CH(CH₃)— | H | 2F4Br | |
| 189 | O | O | O | CH₃ | H | H | —CH(CH₃)— | H | 2I4Cl | |
| 190 | O | O | O | CH₃ | H | H | —CH(CH₃)— | H | 2Cl4CH₃ | 120–122 |
| 191 | O | O | O | CH₃ | H | H | —CH(CH₃)— | H | 2Br4CH₃ | |
| 192 | O | O | O | CH₃ | H | H | —CH(CH₃)— | H | 2Cl4CF₃ | 103–105 |
| 193 | O | O | O | CH₃ | H | H | —CH(CH₃)— | H | 4CF₃ | |
| 194 | O | O | O | CH₃ | H | H | —CH(CH₃)— | H | 3OCHF₂ | |
| 195 | O | O | O | CH₃ | H | H | —CH(CH₃)— | H | 3OCF₂CHF₂ | |
| 196 | O | O | O | CH₃ | H | H | —CH(CH₃)— | H | 3C₂H₅ | |
| 197 | O | O | O | CH(CH₂F)₂ | H | H | —CH(CH₃)— | H | 2,5(CH₃)₂4Cl | |
| 198 | O | O | O | CH₃ | H | H | —CH(CH₃)— | H | 2,6Cl₂4CF₃ | |
| 199 | O | O | O | C₂H₅ | H | H | —CH(CH₃)— | H | 2,3,4,5,6Cl₅ | |
| 200 | O | O | O | CH₃ | H | H | —CH(CH₃)— | H | 2,4Cl₂3CH₃ | |
| 201 | O | O | O | CH₃ | H | H | —CH(CH₃)— | 4F | 2,4Cl₂ | |
| 202 | O | O | O | CH₃ | H | H | —CH(CH₃)— | H | 2,4Cl₂ | 144–146 |
| 203 | S | O | O | CH₃ | H | H | —CH(CH₃)— | H | 2CF₃ | 98–99 |
| 204 | O | O | O | C₂H₅ | H | H | —CH(CH₃)— | H | 2,4Cl₂ | 106–109 |
| 205 | S | O | O | CH₃ | H | H | —CH(CH₃)— | H | 4CH₃ | 118–121 |
| 206 | O | O | O | CH₃ | H | H | —(CH₂)₂— | H | 4Cl | 160–162 |
| 207 | S | O | O | CH₃ | H | H | —CH(CH₃)— | H | 2Cl | 110–112 |
| 208 | O | O | O | CH₃ | H | H | —CH(CH₃)— | H | 3Br | 112–114 |
| 209 | S | O | O | CH₃ | H | H | —(CH₂)₂— | H | 2Br | |
| 210 | O | O | O | CH₃ | H | H | —CH(CH₃)— | H | 3NO₂ | 140–142 |
| 211 | O | O | O | i-C₃H₇ | H | H | —CH(CH₃)— | H | 2NO₂ | 152–154 |
| 212 | O | O | O | i-C₃H₇ | H | H | —CH(CH₃)— | H | 2,5Cl₂ | 144–146 |
| 213 | O | O | O | C₂H₅ | H | H | —CH(CH₃)— | H | 2Br | |
| 214 | O | O | O | CH₃ | H | H | —CH(CH₃)— | H | 2,5Cl₂ | 121–123 |
| 215 | O | O | O | CH₃ | H | H | —CH(CH₃)— | H | 2Br4CF₃ | 144–146 |
| 216 | O | O | O | CH₃ | H | H | —CH(CH₃)— | H | 2Cl4 | viscous oil |
| 217 | O | O | O | i-C₃H₇ | H | H | —CH(CH₃)— | H | 3NO₂4CF₃ | 144–146 |
| 218 | O | O | O | C₂H₅ | H | H | —CH(CH₃)— | H | 2Cl4,5(CH₃)₂ | 128–130 |
| 219 | O | O | O | CH₃ | H | H | —CH(CH₃)— | H | 2,4,5Cl₃ | 126–127 |
| 220 | O | O | O | C₂H₅ | H | H | —CH(CH₃)— | H | 2,5Cl₂ | 120–122 |
| 221 | O | O | O | C₂H₅ | H | H | —CH(CH₃)— | H | 2Cl | |
| 222 | O | O | O | C₂H₅ | H | H | —CH(CH₃)— | H | 3Br | |

-continued

| NO. | A | B | D | R¹ | R² | R³ | R⁴ | X | Y | m.p. °C. |
|---|---|---|---|---|---|---|---|---|---|---|
| 224 | O | O | O | C₂H₅ | H | H | —CH(CH₃)— | H | 2,4,5Cl₃ | 129-131 |
| 225 | O | O | O | C₂H₅ | H | H | —CH(CH₃)— | H | 2Cl4Br | |
| 226 | S | O | O | CH₃ | H | H | —CH(CH₃)— | H | 2,4,5Cl₃ | |
| 227 | O | O | O | i-C₃H₇ | H | H | —CH(CH₃)— | H | 2Cl4Br | |
| 228 | O | O | O | C₂H₅ | H | H | —CH(CH₃)— | H | 2Cl4F | |
| 229 | O | O | O | i-C₃H₇ | H | H | —CH(CH₃)— | H | 2Cl4F | 177-179 |

The compounds of the invention can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvent and/or carriers, with or without the addition of emulsifiers and dispersants and, where water is used as the diluent, with or without organic auxiliary solvents. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g., ethanolamine, dimethylformamide, and water; solid carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The agent in general contain from 0.1 to 95% by weight of active ingredient, preferably from 0.5 to 90%.

The agents, and the ready-to-use preparations obtained therefrom, e.g., solutions, emulsions, suspensions, powders, dusts, pastes or granules, are applied in conventional manner, e.g. by spraying, atomizing, dusting, broadcasting or watering.

EXAMPLES ILLUSTRATING THE HERBICIDAL ACTION

The influence of various representatives of the compounds according to the invention on the growth of unwanted and crop plants in comparison with chemically similar, prior art compounds is demonstrated in the following greenhouse experiments.

The vessels employed were plastic flowerpots having a volume of 300 cm³, and which were filled with a sandy loam containing about 1.5% humus. The seeds of the test plants (cf. Table 1) were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. No cover was placed on the vessels.

The pots were set up in the greenhouse-species from warmer areas at from 25° to 40° C., and species from moderate climates at 15° to 30° C. The experiments were run for from 3 to 6 weeks. During this period, the plants were tended and their reactions to the various treatments assessed. The following tables contain the compounds investigated, the application rates in kg/ha of active ingredient, and the plants used for the tests. The scale used for assessment was 0 to 100, 0 denoting no damage or normal emergence, and 100 denoting nonemergence or complete destruction of at least the visible plant parts.

The following tables demonstrate the selective herbicidal action of the compounds according to the invention. The agents may be applied pre- or postemergence, either to the location before the unwanted plants have germinated or sprouted from vegetative plant parts, or to the leaves of the unwanted and crop plants. A further application technique is to spray the active ingredients with the aid of spraying equipment in such a way that the leaves of sensitive crop plants are if possible not hit; the active ingredients reach the soil or unwanted plants growing below the crop plants (post-directed, lay-by treatment). The application rates vary, depending on season and growth stage, from 0.1 to 15 kg/ha and more; higher rates are particularly suitable for total elimination of vegetation.

In view of the many application methods possible, the agents according to the invention, or mixtures containing them, may be used in addition to the crop plants listed in the tables in a large number of other crops for eliminating unwanted growth.

The following crop plants are given by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Aventa sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* turnips | |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gessypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |

-continued

| Botanical name | Common name |
|---|---|
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum | parsley |
| spp. tuberosum | |
| Picea abies | Norway spruce |
| Abies alba | fir |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Secale cereale | rye |
| Sesamum indicum | sesame |
| Solanum tuberosum | Irish potatoes |
| Sorghum bicolor (s. vulgare) | grain sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguicculata) | cow peas |
| Vitis vinifera | grapes |
| Zea mays | Indian corn, sweet corn, maize |

The new m-anilide-urethanes may be mixed with each other and with numerous representatives of other herbicidal or growth-regulating active ingredient groups. Examples of suitable components for mixtures are diazines, N-phenylcarbamates, thiolcarbamates, diurethanes, halocarboxylic acids, phenoxy fatty acids, triazines, amides, ureas, diphenyl ethers, triazinones, uracils, benzofuran derivatives, etc. These combinations broaden the spectrum of action and in some instances synergistic effects are achieved. A number of active ingredients which, when combined with the new active ingredients, give mixtures suitable for widely varying areas of application are given below by way of example:

| R | R¹ | R² |
|---|---|---|
|  | NH₂ | Cl |
|  | NH₂ | Br |
|  | OCH₃ | OCH₃ |
|  | N(CH₃)₂ | Cl |
|  | OCH₃ | OCH₃ |
|  | NH₂ | Cl |
|  | N(CH₃)₂ | Cl |
|  | NHCH₃ | Cl |
|  | OCH₃ | Cl |
|  | NH₂ | Br |
|  | OCH₃ | OCH₃ |
| F₂CHCF₂O— | NH.CH₃ | Cl |

| R | R¹ | R² | R³ |
|---|---|---|---|
| H | 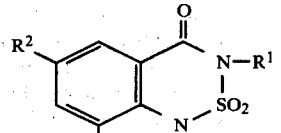 | H | H (salts) |
| H |  | H | CH₃ (salts) |
| H |  | H | Cl (salts) |
| CH₂—OCH₃ |  | H | H |
| H |  | H | F (salts) |

-continued

| | | | |
|---|---|---|---|
| CH₂—OCH₃ | iPr | H | Cl |
| CH₂—OCH₃ | iPr | H | F |
| CN | iPr | H | Cl |

Structure:
R¹, R², R³, R⁴, R substituents on benzene with 2,6-dinitro and N(R³)(R⁴) group

| R | R¹ | R² | R³ | R⁴ |
|---|---|---|---|---|
| H | H₃CSO₂ | H | n.C₃H₇ | n.C₃H₇ |
| H | F₃C | H | C₂H₅ | C₄H₉ |
| H | F₃C | H | n.C₃H₇ | n.C₃H₇ |
| H | F₃C | H | —CH₂—CH₂Cl | n.C₃H₇ |
| H | tert.C₄H₉ | H | sec.C₄H₉ | sec.C₄H₉ |
| H | SO₂NH₂ | H | n.C₃H₇ | n.C₃H₇ |
| H | F₃C | H | n.C₃H₇ | —CH₂-cyclopropyl |
| H₃C | H₃C | H | H | sec.C₄H₉ |
| H₃C | H₃C | H | H | —CH(C₂H₅)₂ |
| H | F₃C | NH₂ | n.C₃H₇ | n.C₃H₇ |
| H | H₃C | H | n.C₃H₇ | n.C₃H₇ |
| H | iC₃H₇ | H | n.C₃H₇ | n.C₃H₇ |

Structure: R(R²)N—C(=O)—O—R²  (carbamate: R¹, R²)

| R | R¹ | R² |
|---|---|---|
| phenyl | H | iC₃H₇ |
| CH₃ | H | —CH₂-(3,4-diCl-phenyl) |
| 3-Cl-phenyl | H | —CH(CH₃)—C≡CH |
| 3-Cl-phenyl | H | —CH₂—C≡C—CH₂Cl |
| 3-Cl-phenyl | H | iC₃H₇ |

-continued

| | | |
|---|---|---|
| phenyl | H | —CH(CH₃)—C(=O)—NH—C₂H₅ |
| 2,3-diCl-phenyl (ortho-Cl shown) | H | CH₃ |
| 4-H₂N-phenyl-SO₂— | H | CH₃ |
| CH₃ | H | tert.C₄H₉ (2,6-di-tert-butyl-4-methylphenyl) |
| phenyl | H | —N=C(CH₃)₂ |

Structure: R—N(R¹)—C(=O)—O—(phenyl)—NH—C(=O)—O—R²

| R | R¹ | R² |
|---|---|---|
| 3-CH₃-phenyl | H | CH₃ |
| phenyl | H | C₂H₅ |
| 3,5-diCH₃-phenyl | H | C₂H₅ |
| phenyl | CH₃ | CH₃ |
| 4-F-phenyl | H | CH₃ |
| 3,4-diF-phenyl | H | C₂H₅ |
| 3-Cl-4-F-phenyl | H | C₂H₅ |
| 3,4-diF-phenyl | H | CH₃ |

-continued

| Structure | | |
|---|---|---|
| 3-fluoro-4-chlorophenyl group | H | CH₃ |
| 3-CF₃-phenyl-NH-C(O)-O-(2-methyl-5-NHC(O)OCH₃-phenyl) | | |

$$\begin{array}{c} R^1 \\ | \\ R-N-C-S-R^2 \\ \phantom{R-N-}\overset{\|}{O} \end{array}$$

| R | R¹ | R² |
|---|---|---|
| iC₃H₇ | iC₃H₇ | CH₂—CCl=CCl₂ |
| iC₃H₇ | iC₃H₇ | CH₂—CCl=CHCl |
| n.C₃H₇ | n.C₃H₇ | C₂H₅ |
| cyclohexyl | C₂H₅ | C₂H₅ |
| sec.C₄H₉ | sec.C₄H₉ | C₂H₅ |
| n.C₃H₇ | n.C₃H₇ | n.C₃H₇ |
| C₂H₅ | C₂H₅ | —CH₂—C₆H₄—Cl |
| sec.C₄H₉ | sec.C₄H₅ | —CH₂—C₆H₅ |
| norbornyl-methyl | C₂H₉ | C₂H₅ |
| iC₃H₇ | iC₃H₇ | —CH₂-isoxazoline(3-CH₃) |
| iC₃H₇ | iC₃H₇ | —CH₂-isoxazoline(3-C₂H₅) |

$$\begin{array}{c} CH_3 \\ (CH_3)_2CHCH_2-C(CH_3)_2-N-C-S-R \\ \phantom{(CH_3)_2CHCH_2-C(CH_3)_2-N-}\overset{\|}{O} \end{array}$$

| R |
|---|
| —CH₂—CCl=CHCl |
| —CH₂—CCl=CCl₂ | hexamethyleneimine-N-C(O)-S-C₂H₅

$$\begin{array}{c} X \\ | \\ R-C-C-O-R^1 \\ | \phantom{-}\overset{\|}{O} \\ Y \end{array}$$

| R | X | Y | R¹ |
|---|---|---|---|
| CH₃ | | | Cl Cl Na |
| 4-Cl-C₆H₄-CH₂— | | | Cl H CH₃ |
| C₆H₅-C(O)-HNO— | | | H H H (salts) |
| Cl | | | Cl Cl Na |
| 4-Cl-C₆H₄-O-C₆H₄-O— | | | H CH₃ CH₃ |
| C₆H₅-C(O)-N(3,4-diCl-C₆H₃)- | | | H CH₃ C₂H₅ |
| C₂H₅ | | | Cl Cl Na |
| C₆H₅-C(O)-N(3-Cl-4-F-C₆H₃)- | | | H CH₃ iC₃H₇ |
| C₆H₅-C(O)-N(4-Cl-2-F-C₆H₃)- | | | H CH₃ CH₃ |
| 4-Cl-C₆H₄-O-C₆H₄-O— | | | H CH₃ —CH₂-CH(CH₃)₂ |
| 3,5-diCl-pyridinyl-2-O-C₆H₄-O— | | | H CH₃ Na |
| 2-Cl-4-CF₃-C₆H₃-O-C₆H₄-O— | | | H CH₃ Na |
| 4-CF₃-C₆H₄-O-C₆H₄-O— | | | H CH₃ CH₃ |

$$\begin{array}{c} X \\ \phantom{xx} N \\ R^1 \diagdown N \diagup \diagdown N \diagup R^2 \\ | \phantom{xxxxxxxxxx} | \\ R \phantom{xxxxxxxxxxx} R^3 \end{array}$$

| R | R¹ | X | R² | R³ |
|---|---|---|---|---|
| H | tert.C₄H₉ | SCH₃ | H | C₂H₅ |
| H | C₂H₅ | SCH₃ | H | C₂H₅ |
| H | iC₃H₇ | SCH₃ | H | C₂H₅ |
| H | CH₃ | SCH₃ | H | iC₃H₇ |

4,373,105

-continued

| | | | | |
|---|---|---|---|---|
| H | iC$_3$H$_7$ | Cl | H | C$_2$H$_5$ |
| H | iC$_3$H$_7$ | Cl | H | cyclopropyl |
| H | C$_2$H$_5$ | Cl | H | C$_2$H$_5$ |
| H | C$_2$H$_5$ | Cl | H | —C(CH$_3$)$_2$—CN |
| H | iC$_3$H$_7$ | Cl | H | iC$_3$H$_7$ |
| H | iC$_3$H$_7$ | OCH$_3$ | H | iC$_3$H$_7$ |
| H | NC—C(CH$_3$)$_2$— | Cl | H | cyclopropyl |
| H | C$_2$H$_5$ | Cl | H | —CH(CH$_3$)—CH$_2$—OCH$_3$ |
| H | C$_2$H$_5$ | Cl | H | —CH(CH$_3$)—C≡CH |

$$\begin{array}{c} R^1 \\ | \\ N-C-R^2 \\ | \quad \| \\ R \quad O \end{array}$$

| R | R$^1$ | R$^2$ |
|---|---|---|
| CH$_3$ | CH$_3$ | CH(C$_6$H$_5$)$_2$ |
| 1-naphthyl | H | 2-HOOC—C$_6$H$_4$— |
| 3,4-Cl$_2$—C$_6$H$_3$— | H | cyclopropyl |
| 3,4-Cl$_2$—C$_6$H$_3$— | H | C$_2$H$_5$ |
| 4-methyl-5-chloro-thiazol-2-yl | H | C$_2$H$_5$ |
| 4-Cl—C$_6$H$_4$— | H | —C(CH$_3$)$_2$—CH$_2$—CH$_2$—CH$_3$ |
| C$_6$H$_5$— | —CH(CH$_3$)—C≡CH | CH$_2$Cl |
| 2-CH$_3$-6-C$_2$H$_5$—C$_6$H$_3$— | —CH(CH$_3$)—CH$_2$—OCH$_3$ | CH$_2$Cl |

-continued

| R | R$^1$ | R$^2$ |
|---|---|---|
| 2,6-(C$_2$H$_5$)$_2$—C$_6$H$_3$— | —CH$_2$—OCH$_3$ | CH$_2$Cl |
| 2,6-(C$_2$H$_5$)$_2$—C$_6$H$_3$— | —CH$_2$—C(=O)—OC$_2$H$_5$ | CH$_2$Cl |
| C$_6$H$_5$— | iC$_3$H$_7$ | CH$_2$Cl |
| 2,6-(CH$_3$)$_2$—C$_6$H$_3$— | —CH$_2$—O—CH$_2$—CH(CH$_3$)—CH$_3$ | CH$_2$Cl |
| 2,6-(C$_2$H$_5$)$_2$—C$_6$H$_3$— | —CH$_2$—O—C$_4$H$_9$n. | CH$_2$Cl |
| 2,6-(CH$_3$)$_2$—C$_6$H$_3$— | —CH$_2$—O—C$_2$H$_5$ | CH$_2$Cl |
| 2,6-(CH$_3$)$_2$—C$_6$H$_3$— | —CH$_2$—(1,3-dioxolan-2-yl) | CH$_2$Cl |
| 2,6-(CH$_3$)$_2$—C$_6$H$_3$— | —CH$_2$—CH$_2$—OCH$_3$ | CH$_2$Cl |
| 2,6-(CH$_3$)$_2$—C$_6$H$_3$— | —CH$_2$—N(4-methylpyrazol-1-yl) | CH$_2$Cl |
| 2,6-(CH$_3$)$_2$—C$_6$H$_3$— | —CH$_2$—N(3-methoxypyrazol-1-yl) | CH$_2$Cl |
| 2,6-(CH$_3$)$_2$—C$_6$H$_3$— | —CH$_2$—N(pyrazol-1-yl) | CH$_2$Cl |

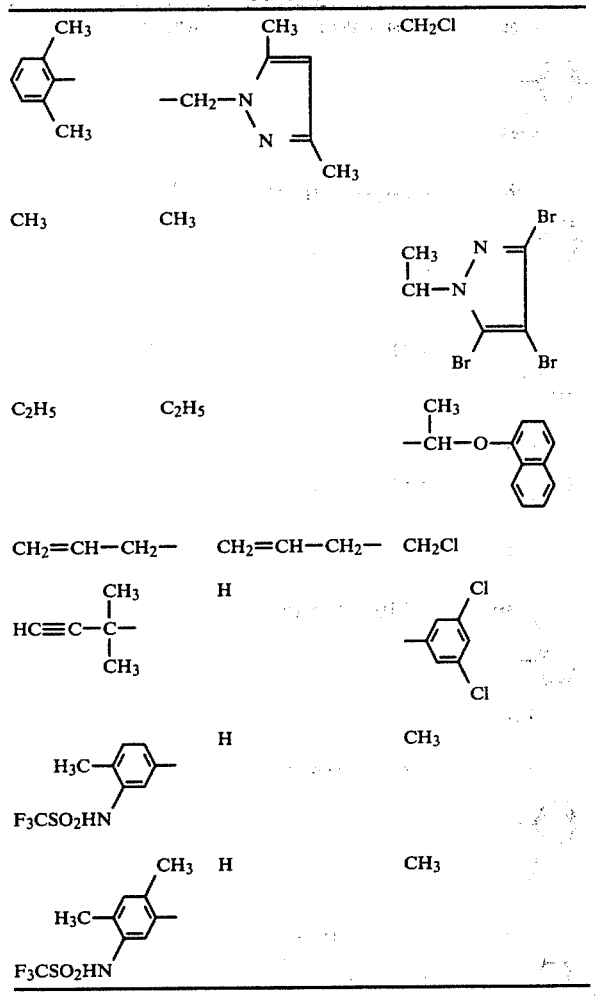
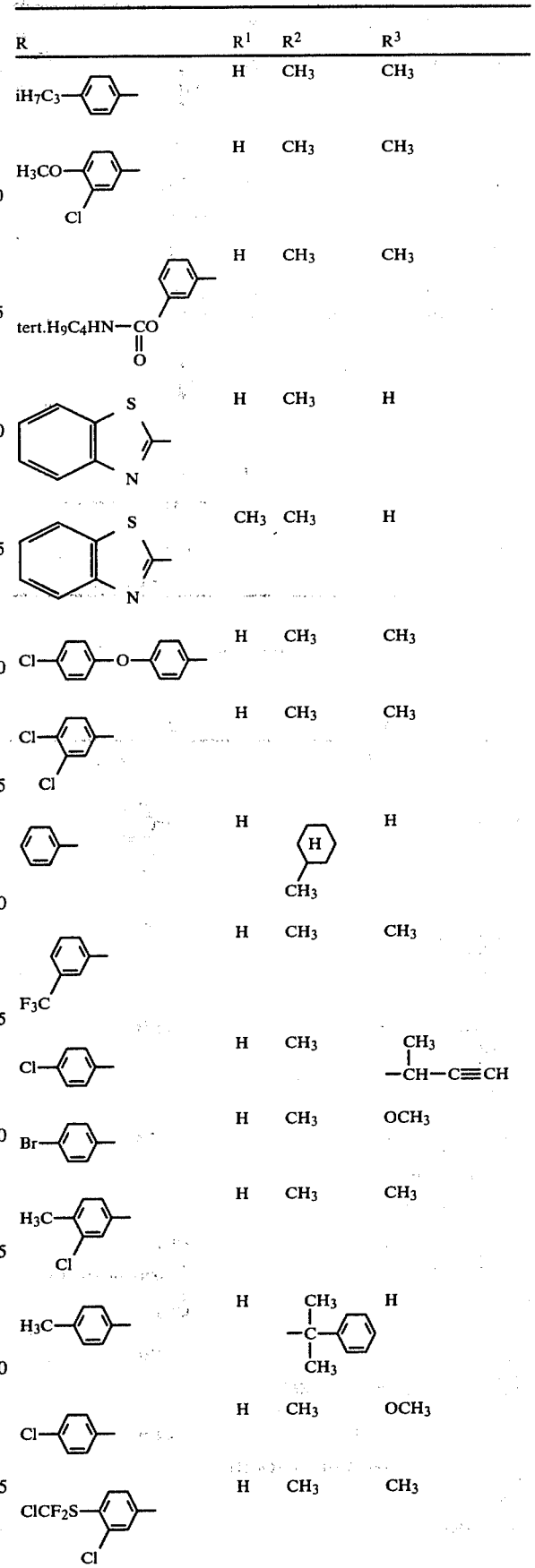

-continued

| Structure | | | |
|---|---|---|---|
| phenyl | H | CH₃ | CH₃ |
| 4-Cl-phenyl | H | CH₃ | CH₃ |
| cycloheptyl (H) | H | CH₃ | CH₃ |
| 3,4-diCl-phenyl | H | CH₃ | OCH₃ |
| 3-Cl-4-Br-phenyl | H | CH₃ | OCH₃ |
| 3,4-diCl-phenyl | H | CH₃ | H |
| tert.H₉C₄—[thiadiazole]— | CH₃ | CH₃ | H |
| F₃C—[thiadiazole]— | CH₃ | CH₃ | H |
| 3,4-diCl-phenyl | H | C₂H₅ | C₂H₅ |
| F₂CHCF₂O-phenyl | H | CH₃ | CH₃ |
| H₃CO, Cl-phenyl | H | CH₃ | OCH₃ |
| Cl, H₃CO, Cl-phenyl | H | CH₃ | CH₃ |

HN—[ring]—N—C(=O)—NH—CH₂—CH(CH₃)₂
         ‖
         O

-continued

| R | R¹ | R² | R³ |
|---|---|---|---|
| Cl | Cl | Cl | H |
| F | Cl | Cl | H |
| NO₂ | CF₃ | H | H |
| Cl | CF₃ | H | COOH (salts) |
| Cl | Cl | H | H |
| Cl | Cl | H | OCH₃ |
| Cl | Cl | H | —C(=O)—OCH₃ |
| H | CF₃ | Cl | H |
| H | CF₃ | Cl | OC₂H₅ |

| R | R¹ | R² |
|---|---|---|
| tert.C₄H₉ | NH₂ | SCH₃ |
| tert.C₄H₉ | —N=CH—CH(CH₃)₂ | SCH₃ |
| phenyl | NH₂ | CH₃ |

| R | R¹ | R² | R³ |
|---|---|---|---|
| H | CH₃ | Br | —CH(CH₃)—C₂H₅ |
| H | CH₃ | Br | iC₃H₇ |
| H | CH₃ | Cl | tert.C₄H₉ |
| H | CH₃ | Cl | tetrahydropyranyl |

| R | R¹ | R² | R³ |

-continued

| Structure | R | R¹ | R² |
|---|---|---|---|
| —C(O)—CH₃ | sec.C₄H₉ | H | H |
| H | CH₃ | H | H (salts, esters) |
| H | sec.C₄H₉ | H | H (salts, esters) |
| —C(O)—CH₃ | tert.C₄H₉ | H | H |
| —C(O)—CH₃ | tert.C₄H₉ | H | CH₃ |
| H | iC₃H₇ | CH₃ | H (salts, esters) |
| H | tert.C₄H₉ | H | H (salts) |

Structure: Y,X-phenyl-N-(ring with C=O, N-R, C=O, O)

| X | Y | R |
|---|---|---|
| CF₃ | H | CH₃ |
| H | F | CH₃ |

Structure: benzoxazine with N=C-phenyl and C=O

Structure: R-SO₂-phenyl-O-dihydrofuran with C(CH₃)₂, CH, OR¹

| R | R¹ |
|---|---|
| CH₃ | C₂H₅ |
| (CH₃)₂N— | C₂H₅ |
| CH₃C(O)N(CH₃)— | C₂H₅ |

Structure: hydantoin-like ring R-N—O, C=O, N-R¹, C=O

| R | R¹ |
|---|---|
| 3,4-dichlorophenyl | CH₃ |
| 3-(iH₇C₃HN—C(O)—)phenyl | CH₃ |

-continued

Structure: 3-methyl-phenyl-NH-C(O)-O-tert.C₄H₉

Structure: pyrazolidinium cation with R², R on C, two phenyl groups, N-R¹, N-R² ⊕ X⁻

| R | R¹ | R² | X |
|---|---|---|---|
| CH₃ | CH₃ | H | H₃C-C₆H₄-SO₃⁻ (tosylate) |
| CH₃ | CH₃ | Br | CH₃OSO₂O |
| CH₃ | CH₃ | CH₃ | CH₂OSO₂—O |
| CH₃ | CH₃ | CH₃ | CF₃—SO₂ |

Structure: diketone with =C(C₂H₅)(NH—O—C₂H₅), C₂H₅, O

Structure: 5,5-dimethylcyclohexane-1,3-dione with =C(n.C₃H₇)(NH—O—CH₂—CH=CH₂)

Structure: 5,5-dimethyl-4-hydroxy-cyclohex-3-ene with C(n.C₃H₇)=N—O—CH₂—CH=CH₂, 2-oxo, 6-C(O)—O—CH₃

Structure: same as above with ONa instead of OH

Structure: phenyl-C(OH)=CH-C(Cl)=N-N= (hydrazone, salts, esters)

Structure: benzene with R, R¹, R², R³, R⁴ substituents

| R | R¹ | R² | R³ | R⁴ |
|---|---|---|---|---|
| Cl | Cl | NH₂ | Cl | COOH (salts, esters) |

-continued

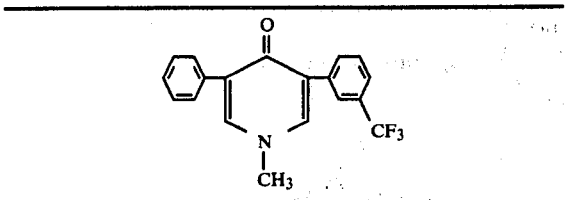

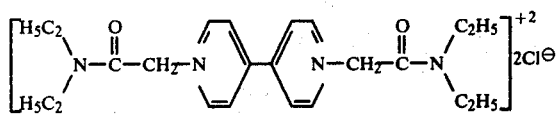

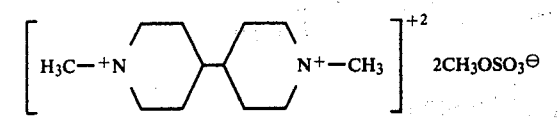

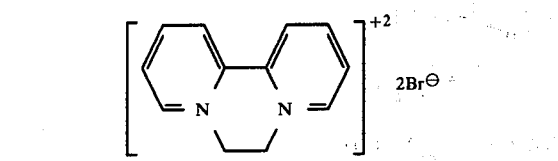

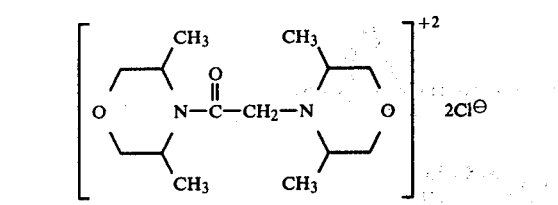

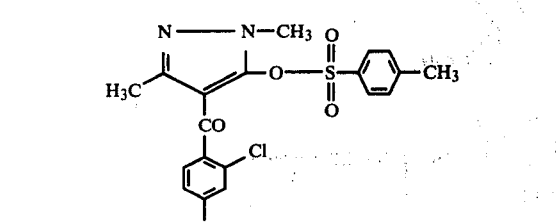

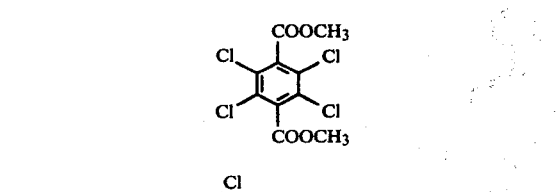

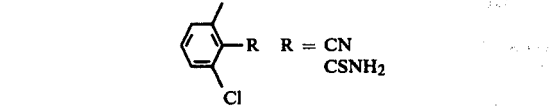

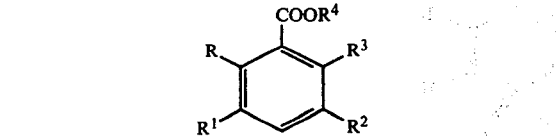

| R | R¹ | R² | R³ | R⁴ |
|---|----|----|----|-----|
| H | Cl | NH₂ | Cl | H (salts, esters, amides) |
| Cl | Cl | H | Cl | Na |
| H | I | I | I | H |
| Cl | H | Cl | OCH₃ | H |
| Cl | Cl | H | Cl | H.(CH₃)₂NH |

-continued

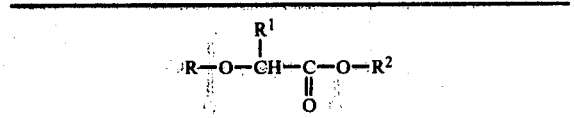

| R | R¹ | R² | |
|---|----|----|---|
| 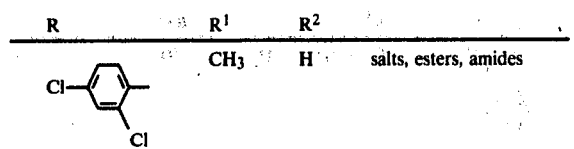 | CH₃ | H | salts, esters, amides |
|  | H | H | salts, esters, amides |
|  | H | H | salts, esters, amides |
| 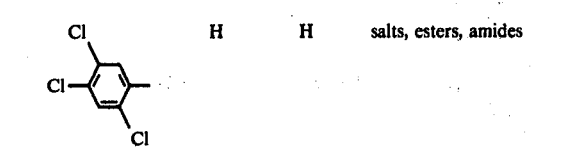 | H | H | salts, esters, amides |
|  | CH₃ | H | salts, esters, amides |
|  | CH₃ | H | salts, esters, amides |

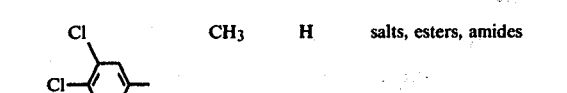

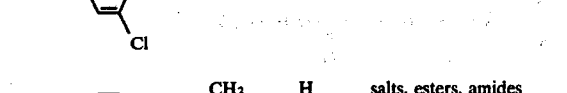 salts, esters, amides

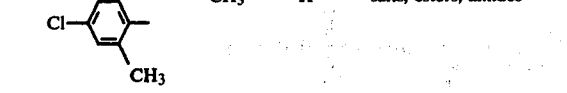 salts, esters, amides

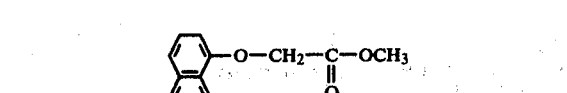 salts, esters, amides

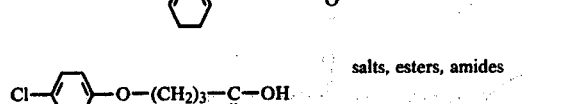

| R | R¹ | R² |
|---|----|----|
| OH | CH₃ | Na |
| CH₃ | CH₃ | Na |
| CH₃ | CH₃ | OH |
| ONa | CH₃ | Na |

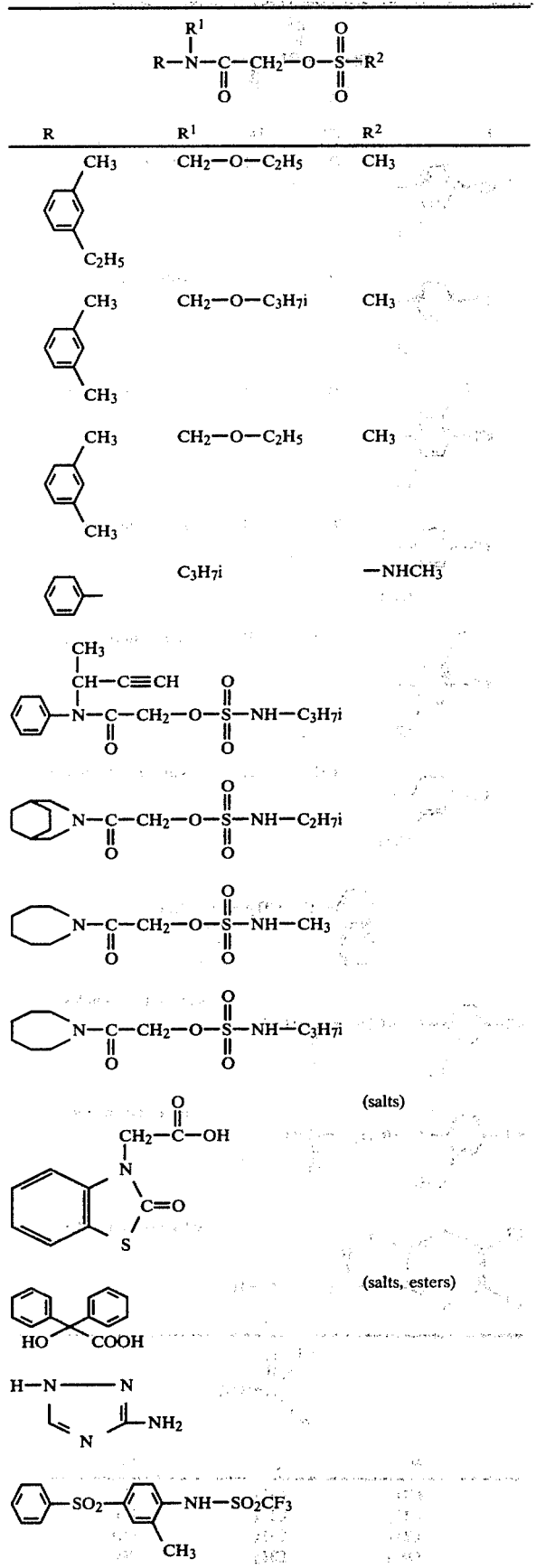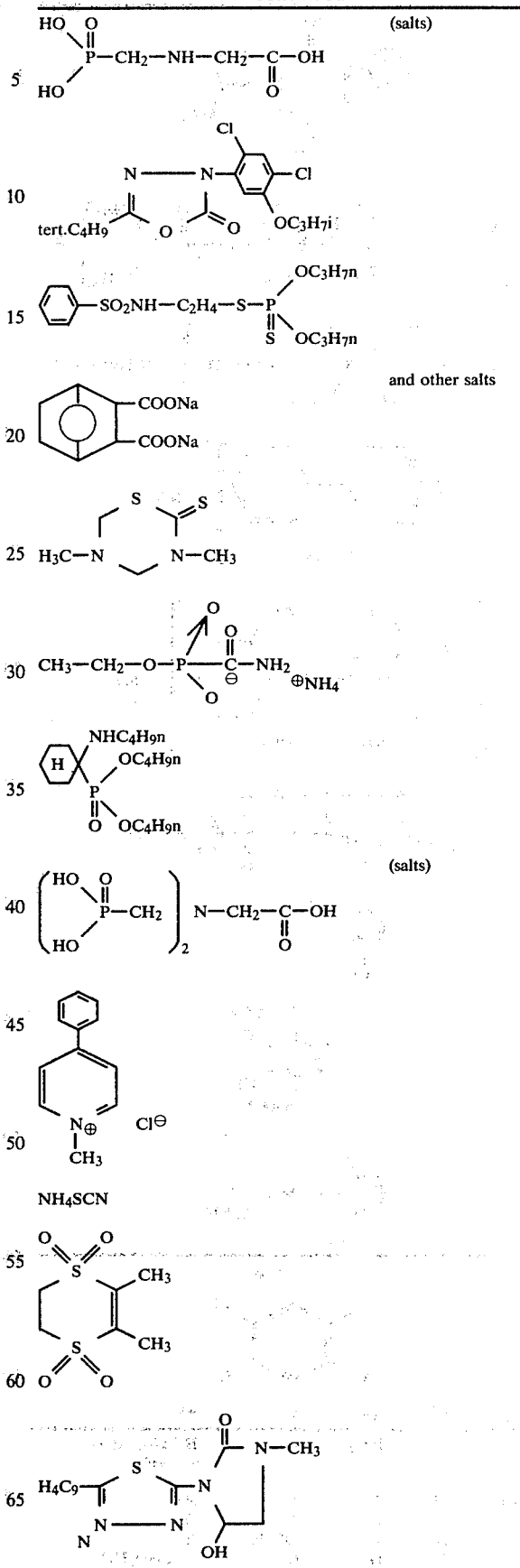

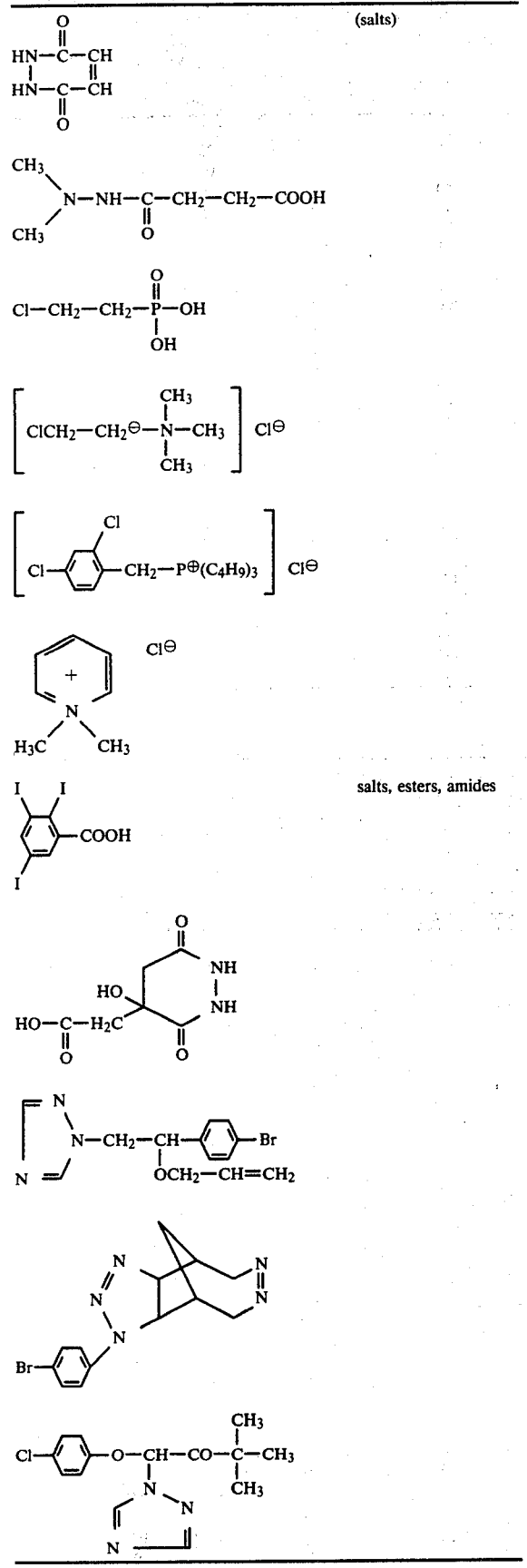

It may also be useful to apply the new compounds, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies. Oils of various types, wetting agents, spreader-stickers and antifoams may also be added to the individual active ingredients or mixtures thereof.

TABLE 1

List of plant names

| Botanical name | Common name |
|---|---|
| Amaranthus retroflexus | redroot pigweed |
| Arachys hypogaea | peanuts (groundnuts) |
| Beta vulgaris | sugarbeets |
| Cassia tora | |
| Centaurea cyanus | cornflower |
| Chenopodium album | lambsquarters (goosefoot) |
| Cyperus ferax | |
| Echinochloa crus galli | barnyardgrass |
| Euphorbia geniculata | South American member of the spurge family |
| Glycine max | soybeans |
| Gossypium hirsutum | cotton |
| Hordeum vulgare | barley |
| Ipomoea spp. | morningglory |
| Lamium spp. | dead-nettle |
| Matricaria spp. | chamomille |
| Oryza sativa | rice |
| Polygonum persicaria | ladysthumb |
| Sesbania exaltata | hemp sesbania (coffeeweed) |
| Sinapis alba | white mustard |
| Sorghum bicolor | wild cane (grain sorghum) |
| Triticum aestivum | wheat |
| Zea mays | Indian corn |
| Mentha piperita | peppermint |
| Galium aparine | catchweed bedstraw |

TABLE 2

Herbicidal action of the novel compounds on preemergence application in the greenhouse

| Compound no. | kg/ha | Test plant: Sinapis alba % damage |
|---|---|---|
| 157 | 3.0 | 100 |
| 57 | 3.0 | 80 |
| 1 | 3.0 | 100 |
| 149 | 3.0 | 90 |
| 5 | 3.0 | 90 |
| 40 | 3.0 | 100 |
| 3 | 3.0 | 100 |
| 6 | 3.0 | 100 |
| 41 | 3.0 | 90 |
| 12 | 3.0 | 100 |
| 32 | 3.0 | 80 |
| 38 | 3.0 | 100 |
| 28 | 3.0 | 100 |
| 60 | 3.0 | 100 |
| 17 | 3.0 | 90 |
| 89 | 3.0 | 90 |
| 53 | 3.0 | 90 |
| 65 | 3.0 | 90 |
| 52 | 3.0 | 90 |
| 70 | 3.0 | 80 |
| 133 | 3.0 | 100 |
| 4 | 3.0 | 100 |
| 71 | 3.0 | 90 |
| 61 | 3.0 | 100 |
| 120 | 3.0 | 100 |
| 117 | 3.0 | 90 |
| 2 | 3.0 | 100 |
| 168 | 3.0 | 90 |
| 99 | 3.0 | 90 |
| 94 | 3.0 | 90 |
| 150 | 3.0 | 90 |
| 128 | 3.0 | 90 |
| 36 | 3.0 | 100 |

TABLE 2-continued

Herbicidal action of the novel compounds on preemergence application in the greenhouse

| Compound no. | kg/ha | Test plant: Sinapis alba % damage |
|---|---|---|
| 193 | 3.0 | 100 |
| 131 | 3.0 | 100 |
| 178 | 3.0 | 100 |
| 179 | 3.0 | 100 |
| 136 | 3.0 | 100 |
| 152 | 3.0 | 100 |
| 202 | 3.0 | 90 |
| 113 | 3.0 | 100 |
| 172 | 3.0 | 90 |
| 158 | 3.0 | 100 |
| 160 | 3.0 | 100 |
| 205 | 3.0 | 90 |
| 66 | 3.0 | 80 |
| 15 | 3.0 | 90 |
| 112 | 3.0 | 90 |
| 142 | 3.0 | 100 |
| 204 | 3.0 | 80 |

TABLE 3

Herbicidal action of the novel compounds on postemergence treatment in the greenhouse

| Compound no. | kg/ha | Centaurea cyanus | Ipomea spp. |
|---|---|---|---|
| 57 | 3.0 | 90 | 100 |
| 1 | 3.0 | 100 | 100 |
| 85 | 3.0 | 70 | 100 |
| 17 | 3.0 | 90 | 90 |
| 89 | 3.0 | 100 | 100 |
| 53 | 3.0 | 100 | 100 |
| 65 | 3.0 | 90 | 100 |
| 58 | 3.0 | 100 | 100 |
| 50 | 3.0 | 100 | 100 |
| 70 | 3.0 | 60 | 90 |
| 71 | 3.0 | 90 | 100 |
| 61 | 3.0 | 60 | 100 |
| 67 | 3.0 | 90 | 100 |
| 82 | 3.0 | — | 100 |
| 106 | 3.0 | 100 | 100 |
| 120 | 3.0 | 100 | 100 |
| 90 | 3.0 | 100 | 90 |
| 94 | 3.0 | 100 | 100 |
| 119 | 3.0 | — | 100 |
| 168 | 3.0 | — | 100 |
| 159 | 3.0 | 100 | 60 |
| 179 | 3.0 | 100 | 100 |
| 136 | 3.0 | 100 | 100 |
| 97 | 3.0 | 80 | 100 |
| 125 | 3.0 | 100 | 90 |
| 191 | 3.0 | 100 | — |
| 160 | 3.0 | 100 | 70 |
| 146 | 3.0 | 90 | 80 |
| 204 | 3.0 | 100 | — |
| 193 | 3.0 | 100 | 100 |
| 187 | 3.0 | 100 | 100 |
| 218 | 3.0 | 100 | 90 |
| 216 | 3.0 | 100 | 100 |
| 217 | 3.0 | 90 | 80 |

TABLE 4

Selective control of unwanted plants in soybeans and cotton; postemergence treatment in the greenhouse

| Compound no. | kg/ha | Glycine max | Goosypium-hirsutum | Oryza nativa | Amaranthus-retroflexus | Chenopodium-album | Euphorbia geniculata | Sesbania exaltata |
|---|---|---|---|---|---|---|---|---|
| 52 | 0.5 | 15 | 0 | 0 | 100 | 100 | 100 | 94 |
| 77 | 0.5 | — | 15 | 0 | 80 | — | — | 80 |
| [structure: CH₃₂N-C(O)-NH-C₆H₄-CH(N-COCH₂-O-C₆H₃Cl₂)] DE-AS 1,793,226 | 0.5 | 90 | 8 | 10 | 0 | 100 | — | 100 |
| [structure: benzisothiazolinone-dioxide with N-C₃H₇i] German 1,542,836 | 0.5 | 0 | 33 | 6 | 35 | 72 | 0 | 44 |
| 65 | 1.0 | — | 5 | 0 | 100 | 95 | 100 | 95 |
| 71 | 0.5 | — | 0 | 0 | 100 | 98 | 100 | — |
| 89 | 0.5 | — | 0 | — | 100 | 100 | 100 | 100 |
| 58 | 1.0 | — | 5 | 15 | 100 | 100 | 100 | 80 |
| 57 | 1.0 | — | 0 | 10 | 100 | 80 | 100 | 90 |
| 70 | 2.0 | — | 5 | 10 | 100 | 100 | 100 | 95 |
| 85 | 1.0 | — | 5 | 15 | 100 | 98 | 100 | 90 |
| 67 | 1.0 | — | 0 | 0 | 100 | 98 | 100 | 95 |
| 50 | 0.5 | — | 10 | 10 | 100 | 98 | 100 | 80 |
| 80 | 1.0 | — | 10 | — | 100 | 100 | 100 | 90 |

TABLE 5

Selective control of unwanted plants; postemergence treatment in the greenhouse

| Compound no. | kg/ha | Arachys hypogaea | Hordeum vulgare | Triticum aestivum | Amaranthus retroflexus | Chenopodium album | Lamium spp. | Sesbania exaltata |
|---|---|---|---|---|---|---|---|---|
| 3 | 0.25 | 6 | 5 | 6 | 100 | 100 | 100 | 88 |
| 4 | 0.25 | 20 | 20 | 0 | 100 | 99 | 85 | 80 |
| 28 | 1.0 | 0 | 0 | 0 | 100 | 90 | 100 | 80 |
| 6 | 0.25 | 15 | — | 0 | 100 | 100 | 100 | — |
| 41 | 1.0 | — | 0 | 0 | 100 | 98 | 100 | 80 |
| 25 | 0.5 | 0 | — | 0 | 100 | 100 | 100 | 80 |
| $H_5C_2-\overset{O}{\underset{\|}{C}}-\overset{H}{\underset{\|}{N}}-\underset{O-\overset{O}{\underset{\|}{C}}-\overset{H}{\underset{\|}{N}}-C_3H_7i}{\text{⌬}}$ | 0.5 | 4 | 27 | 33 | 65 | 37 | 100 | 82 |
|  | 1.0 | 11 | 30 | 40 | 70 | 45 | 100 | 100 |

U.S. Pat. No. 3,972,202

TABLE 6

Selective control of unwanted plants; postemergence treatment in the greenhouse

| Compound no. | kg/ha | Gossypium hirsutum | Oryza sativa | Zea mays | Cassia tora | Cyperus ferax | Matricaria spp. | Sesbania exaltata |
|---|---|---|---|---|---|---|---|---|
| 3 | 0.25 | 23 | 18 | 16 | 100 | 70 | 82 | — |
|   | 0.5 | 24 | 24 | 25 | 100 | 86 | 82 | 92 |
| 133 | 0.5 | 0 | 20 | 10 | — | 95 | 100 | 100 |
| 60 | 2.0 | 8 | 10 | 15 | — | 85 | 100 | 100 |

TABLE 7

Selective control of weeds in sugarbeets and sorghum; postemergence treatment in the greenhouse

| Compound no. | kg/ha | Beta vulgaris | Sorghum bicolor | Lamium spp. | Polygonum persicaria |
|---|---|---|---|---|---|
| 174 | 2.0 | 0 | 10 | 80 | 100 |
| 157 | 1.0 | 0 | 15 | 100 | 100 |
| 60 | 2.0 | 0 | 10 | 100 | 100 |

TABLE 8

Herbicidal action on postemergence application in the greenhouse

| Compound no. | kg/ha | Euphorbia geniculat | Galium aparine | Mentha piperita |
|---|---|---|---|---|
| 166 | 3.0 | 90 | — | 90 |
| 128 | 3.0 | 90 | 80 | — |
| 150 | 3.0 | 100 | 70 | 80 |
| 2 | 3.0 | — | — | 100 |
| 148 | 3.0 | 100 | — | — |
| 101 | 3.0 | 80 | — | — |

TABLE 9

Selective herbicidal action on postemergence application in the greenhouse

| Compound no. | kg/ha | Triticum aestivum | Amaranthus retroflexus | Chenopodium spp. | Euphorbia geniculata |
|---|---|---|---|---|---|
| 148 | 1.0 | 15 | 100 | 98 | 86 |
| 120 | 0.5 | 10 | 95 | 80 | 90 |
| 150 | 1.0 | 0 | 100 | 100 | 98 |
| 128 | 0.5 | 0 | 100 | — | 98 |
| 178 | 0.5 | 5 | 95 | 95 | 89 |
| 113 | 0.5 | 10 | 98 | 98 | 100 |
| 172 | 1.0 | 0 | 100 | 98 | — |
| 36 | 0.5 | 0 | 100 | 80 | 98 |

TABLE 9-continued

Selective herbicidal action on postemergence application in the greenhouse

| Compound no. | kg/ha | Triticum aestivum | Amaranthus retroflexus | Chenopodium spp. | Euphorbia geniculata |
|---|---|---|---|---|---|
| 112 | 0.5 | 10 | 100 | 98 | 100 |
| 158 | 0.5 | 5 | 100 | — | 80 |
| 203 | 0.5 | 10 | 100 | 98 | 100 |
| 131 | 1.0 | 10 | — | 98 | 80 |
| 142 | 0.5 | 0 | 100 | 98 | 90 |
| 117 | 1.0 | 10 | 100 | 98 | 82 |
| 166 | 1.0 | 0 | 100 | — | 100 |
| 1 | 0.5 | 10 | 93 | 95 | 100 |
| 17 | 1.0 | 0 | 100 | 80 | — |
| 2 | 0.5 | 10 | 100 | 98 | 100 |
| 15 | 1.0 | 0 | 100 | 95 | — |
| 82 | 1.0 | 0 | — | 90 | 100 |
| 152 | 0.5 | 5 | 100 | 100 | 100 |

EXAMPLE 6

90 Parts by weight of compound 1 is mixed with 10 parts by weight of N-methyl-α-pyrrolidone. A mixture is obtained which is suitable for application in the form of very fine drops.

EXAMPLE 7

20 Parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 8

20 Parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 9

20 Parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 10

20 Parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 11

3 Parts by weight of compound 3 is intimately mixed with 97 parts by weight of particulate kaolin. A dust is obtained containing 3% by weight of the active ingredient.

EXAMPLE 12

30 Parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 13

40 Parts by weight of compound 1 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 14

20 Parts of compound 2 is intimately mixed with 2 parts of the calcium salt of dodecylbenzeresulfonic acid, 3 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. An m-anilide-urethane of the formula

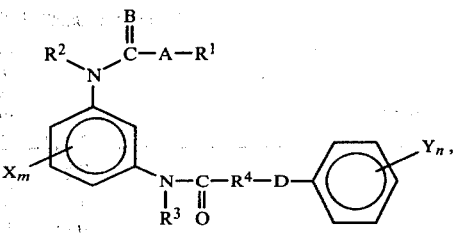

where A and B are identical or different and each denotes oxygen or sulfur, and D is oxygen $R^1$ denotes unsubstituted alkyl; alkyl substituted by halogen, alkoxy, alkoxycarbonyl or cyano; unsubstituted or halogen-substituted alkenyl; unsubstituted or halogen- or alkoxy-substituted alkynyl; or $R^1$ denotes unsubstituted or alkyl-substituted cycloalkyl or aryl, $R^2$ and $R^3$ are identical or different and each denotes hydrogen, alkyl, alkoxyalkyl or haloalkyl, $R^4$ denotes alkylene of 1 to 6 carbon atoms which is unsubstituted or substituted by alkyl, alkoxyalkyl or haloalkyl, X denotes hydrogen, alkyl, haloalkyl, alkoxy, halogen, nitro or amino, Y denotes hydrogen, alkyl, haloalkyl, alkoxyalkyl, cycloalkyl, aralkyl, halogen, or alkenyl chain fused with the benzene ring to give a bromo-substituted or unsubstituted naphthyl ring, Y further denotes alkoxy, haloalkoxy, alkylthio, nitro, aryl, thiocyanato, cyano,

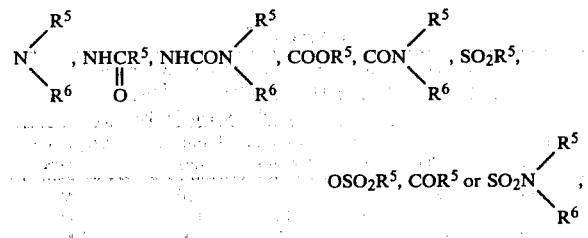

$R^5$ and $R^6$ being identical or different and each denoting hydrogen or having the meanings given for $R^1$, m denotes one of the integers 1, 2, 3 and 4, and n denotes one of the integers 1, 2, 3, 4 and 5.

2. A compound of claim 1 having the formula

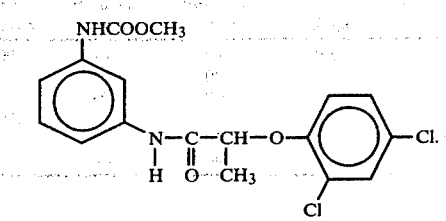

3. An m-anilide-urethane selected from the group consisting of

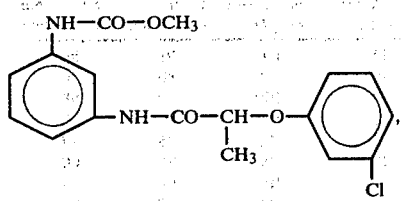

-continued
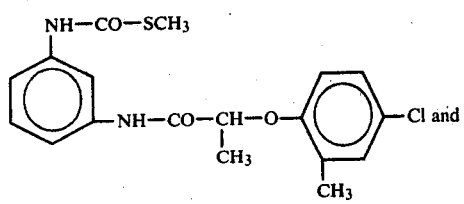
-continued
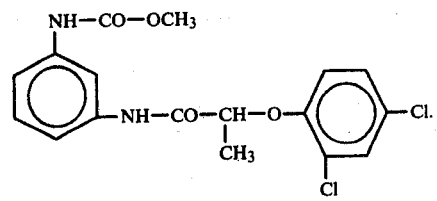
* * * * *